United States Patent [19]

Ashe et al.

[11] Patent Number: 5,600,134
[45] Date of Patent: Feb. 4, 1997

[54] METHOD FOR PREPARING BLEND PRODUCTS

[75] Inventors: Terrence R. Ashe, Point Edward; Robert J. Falkiner, Mississauga; Tian C. Lau, Scarborough, all of Canada

[73] Assignee: Exxon Research and Engineering Company, Florham Park, N.J.

[21] Appl. No.: 494,202

[22] Filed: Jun. 23, 1995

[51] Int. Cl.$^6$ ............................................. H01J 49/00
[52] U.S. Cl. ................................ 250/252.1; 250/288
[58] Field of Search ........................ 250/252.1 R, 288, 250/288 A, 281, 282

[56] References Cited

U.S. PATENT DOCUMENTS

| | | | |
|---|---|---|---|
| 4,251,870 | 2/1981 | Jaffe | 364/500 |
| 4,963,745 | 10/1990 | Maggard | 250/343 |
| 5,072,115 | 12/1991 | Zhou | 250/252.1 R |
| 5,119,315 | 6/1992 | Kemp et al. | 364/498 |
| 5,121,337 | 6/1992 | Brown | 364/498 |
| 5,223,714 | 6/1993 | Maggard | 250/343 |

OTHER PUBLICATIONS 3-100463 Apr. 1991 Takamura et al.

*Primary Examiner*—Jack I. Berman
*Assistant Examiner*—Kiet T. Nguyen
*Attorney, Agent, or Firm*—James H. Takemoto

[57] ABSTRACT

A method for controlling the blending of blend stocks having boiling points less that 350° C. into blend products or controlling refinery or chemical processes with feedstocks and products with boiling points less than 350° C. The method comprises selecting one or more chemical or perceptual or physical property or performance properties of the blend stock or blend product or refinery or chemical feed or product, creating a training set from reference samples which contain characteristic molecular species present in the blend stock or blend product or refinery or chemical process feed or product. The reference samples are subject to GC/MS analysis wherein the often collinear data generated is treated by multivariate correlation methods. The training set produces coefficients which are multiplied by the matrix generated from a GC/MS analysis of an unknown blend stock or blend product or refinery or chemical process feed or product to produce a predicted value for the chemical, performance, perceptual or physical property or groups of properties selected.

11 Claims, 9 Drawing Sheets

MON ERROR

D+L 158 Predicted vs Measured

D+L 302 Predicted vs Measured

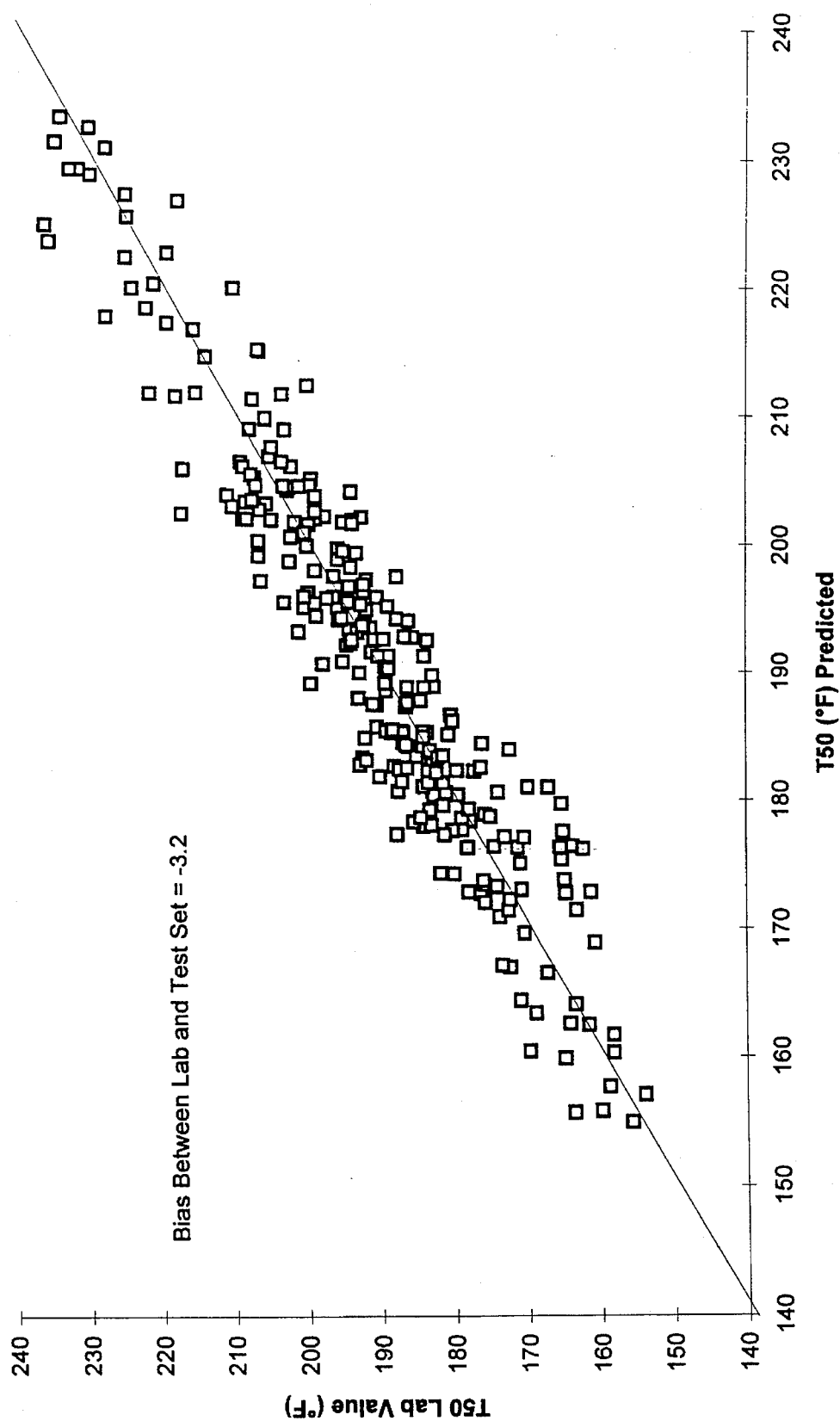

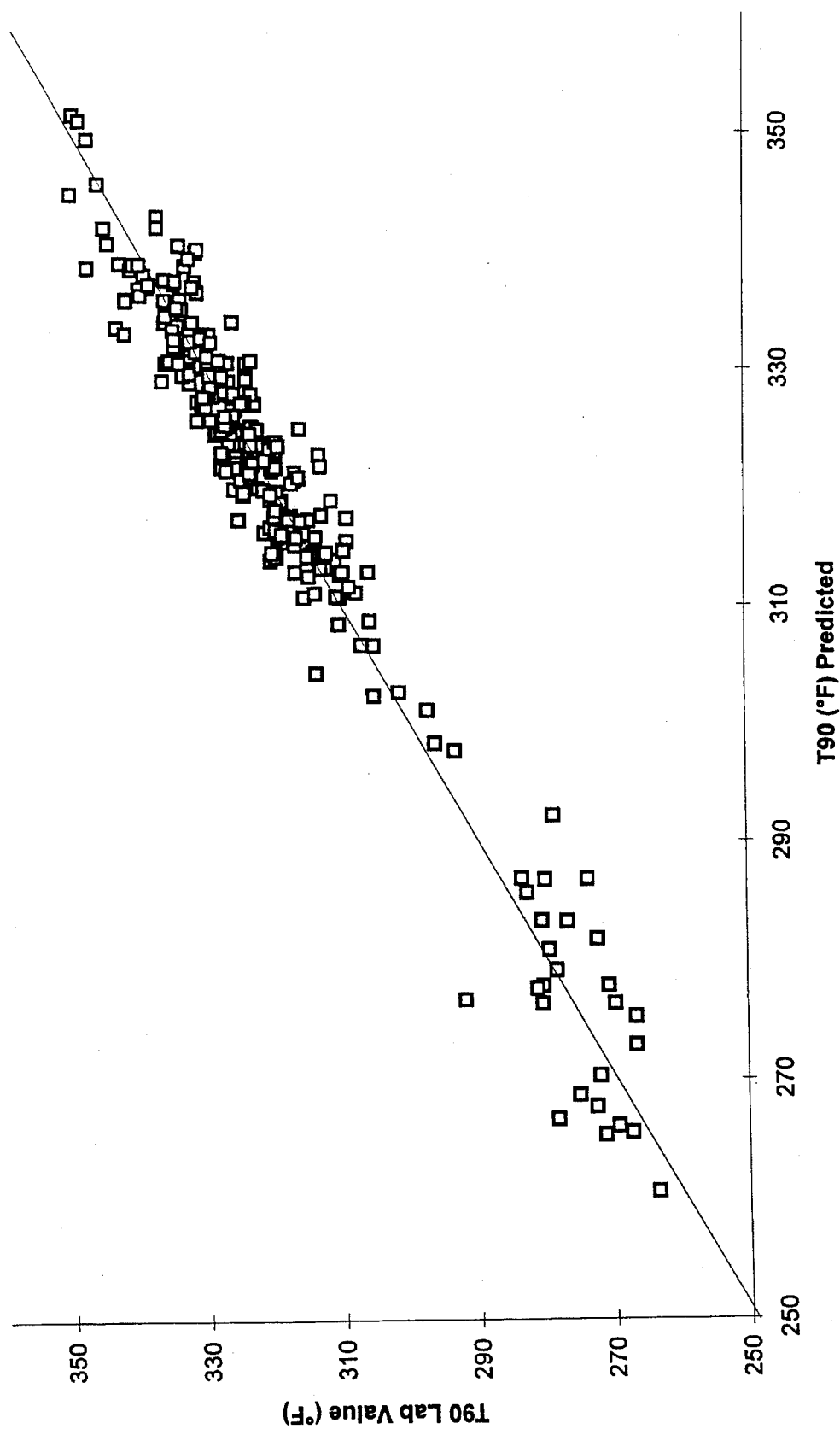

METHOD FOR PREPARING BLEND PRODUCTS

BACKGROUND OF THE INVENTION

1. Field of the Invention

This invention relates to a method for controlling the preparation of blend products from blend stocks boiling at 350° C. or less by predicting chemical, performance, perceptual of physical properties of blend stocks, blend products and/or other refinery or chemical processes using a combination of gas chromatography and mass spectrometry.

2. Description of the Related Art

Refineries and chemical plants typically control blending of various component streams and certain additives through the use of both on-line analyzers and off-line laboratory analyses to provide product quality information. These quality parameters (chemical composition, physical or perceptual or performance properties) are then fed back into linear programs or other blend control software which may be a series of simultaneous equations which predict percentages of refinery streams used to meet certain blend targets. The equations typically are executed more than three times per hour and their output is used to control proportional flow valves to vary the quality of the finished product which can either go to tankage or directly to pipelines and terminals, trucks, or to ship-loading facilities. Multiple on-line analyzers are typically required for blend control.

U.S. Pat. No. 5,223,714 describes a process for controlling the blending of fluids using near-infrared spectroscopy by converting the near-infrared absorbances to signals and mathematically correlating the signal to volume of component.

Gas chromatography has been used to predict physical and performance properties of hydrocarbon mixtures boiling in the gasoline range. Crawford and Hellmuth, Fuel, 1990, 69, 443–447, describe the use of gas chromatography and principal components regression analysis to predict the octane values for gasolines blended from different refinery streams. Japanese laid-open patent application JP 03-100463 relates to a method of estimating the cetane number for fuel oils by separating an oil sample into its components using gas chromatograpy, measuring the signal strength of ion intensities at characteristic masses in the mass spectrum, and correlating these ion intensities to cetane number using multiple regression analysis.

It would be desirable to have a single analyzer means for rapidly measuring the chemical, performance, perceptual or physical properties of blend stocks or blend products and using these properties to control the blending process.

SUMMARY OF THE INVENTION

This invention relates to a process for controlling the blending of a plurality of blend stocks each having boiling points less than about 350° C. into at least one blend product which comprises:

(a) selecting at least one physical, perceptual, performance or chemical property of at least one blend stock or blend product;

(b) selecting reference samples, said reference samples containing characteristic compound types present in at least one blend stock or blend product and which have known values for the property or properties selected in step (a);

(c) producing a training set by the steps of:

(1) injecting each reference sample into a gas chromatograph which is interfaced to a mass spectrometer thereby causing at least a partial separation of the hydrocarbon mixture into constituent chemical components;

(2) introducing the constituent chemical components of each reference sample into the mass spectrometer, under dynamic flow conditions;

(3) obtaining for each reference sample a series of time resolved mass chromatograms;

(4) calibrating the mass chromatograms to correct retention times;

(5) selecting a series of corrected retention time windows;

(6) selecting within each retention time window a series of molecular and/or fragment ions, said ions being representative of characteristic compounds or compound classes expected within the retention time window;

(7) recording the total amount of each characteristic compound or compound group selected in step c(6);

(8) forming the data from steps c(6) and c(7) into a X-block matrix;

(9) forming the property data selected in (a) for reference samples selected in (b) into a Y-block matrix;

(10) analyzing the data from steps c(8) and c(9) by multivariate correlation techniques including Partial Least Squares, Principal Component Regression or Ridge Regression to produce a series of coefficients;

(d) subjecting at least one blend stock or blend product sample to steps c(1) to c(3) in the same manner as the reference sample to produce a series of time resolved mass chromatograms;

(e) repeating steps c(4) to c(8) for each mass chromatogram from step (d);

(f) multiplying the matrix from step (e) by the coefficients from step c(10) to produce a predicted value of the property or properties for the at least one blend stock or blend product sample; and (g) using the predicted values of the property or properties of the at least one blend stock or blend product sample to control the amount of blend stock in the blend product.

In another embodiment, this invention relates to a process for controlling or monitoring chemical or refinery processes which utilize feed stocks and/or produce products having boiling points less than about 350° C. which comprises:

(a) selecting at least one physical, perceptual, performance or chemical property of at least one feed stock or product;

(b) selecting reference samples, said reference samples containing characteristic compound types present in the at least one feed stock or product and which have known values of the property or properties selected in step (a);

(c) producing a training set by the steps of:

(1) injecting each reference sample into a gas chromatograph which is interfaced to a mass spectrometer thereby causing at least a partial separation of the hydrocarbon mixture into constituent chemical components;

(2) introducing the constituent chemical components of each reference sample into the mass spectrometer, under dynamic flow conditions;

(3) obtaining for each reference sample a series of time resolved mass chromatograms;

(4) calibrating the mass chromatograms to correct retention times;

(5) selecting a series of corrected retention time windows;

(6) selecting within each retention time window a series of molecular and/or fragment ions, said ions being representative of characteristic compounds or compound classes expected within the retention time window;

(7) recording the total amount of each characteristic compound or compound group selected in step c(6);

(8) forming the data from steps c(6) and c(7) into a X-block matrix;

(9) forming the property data selected in (a) for reference samples selected in (b) into a Y-block matrix;

(10) analyzing the data from steps c(8) and c(9) by multivariate correlation techniques including Partial Least Squares, Principal Component Regression, or Ridge Regression to produce a series of coefficients;

(d) subjecting at least one refinery or chemical process product or feed stock sample to steps c(1) to c(3) in the same manner as the reference sample to produce a series of time resolved mass chromatograms;

(e) repeating steps c(4) to c(8) for each mass chromatogram from step (d);

(f) multiplying the matrix from step (e) by the coefficients from step c(10) to produce a predicted value of the property or properties for the refinery or chemical process and sample or samples; and (g) using the predicted values of the property or properties of the refinery or chemical sample or samples to control the refinery or chemical process.

The gas chromatography/mass spectrometry (GC/MS) method described above can be used to rapidly predict a wide range of chemical and physical properties of complex mixtures such as blend stocks and blend products. Such properties include octane number, specific chemical constituents, e.g., benzene, $h_2O$ and $h_2S$, additive concentration, distillation characteristics, oxidative stability and the like. The method can also handle the collinear data generated by the GC/MS analyses.

BRIEF DESCRIPTION OF THE DRAWING

FIG. 8 is a graph showing predicted versus measured T50 for the training set.

FIG. 9 is a graph showing predicted versus measured T90 for the training set.

DETAILED DESCRIPTION OF THE INVENTION

The blend products produced by the process of the invention include motor gasoline, aviation gasoline, jet fuel, diesel fuel, heating oil, kerosene, LPG, furnace fuels, solvents, and refinery and/or chemical plant intermediate streams (such as process feed stocks/products). The blend products are produced from various blend stocks which are usually refinery or chemicals streams. Typical blend stocks include reformate, alkylate, isomerates, light cycle oil, catalytic naphthas, raffinates, extracts, virgin distillate streams, gas oils and other refinery or chemical plant intermediate streams or process products; and can include individual components such as additives as well as individual chemicals such as benzene, toluene and xylene.

Figure 1:
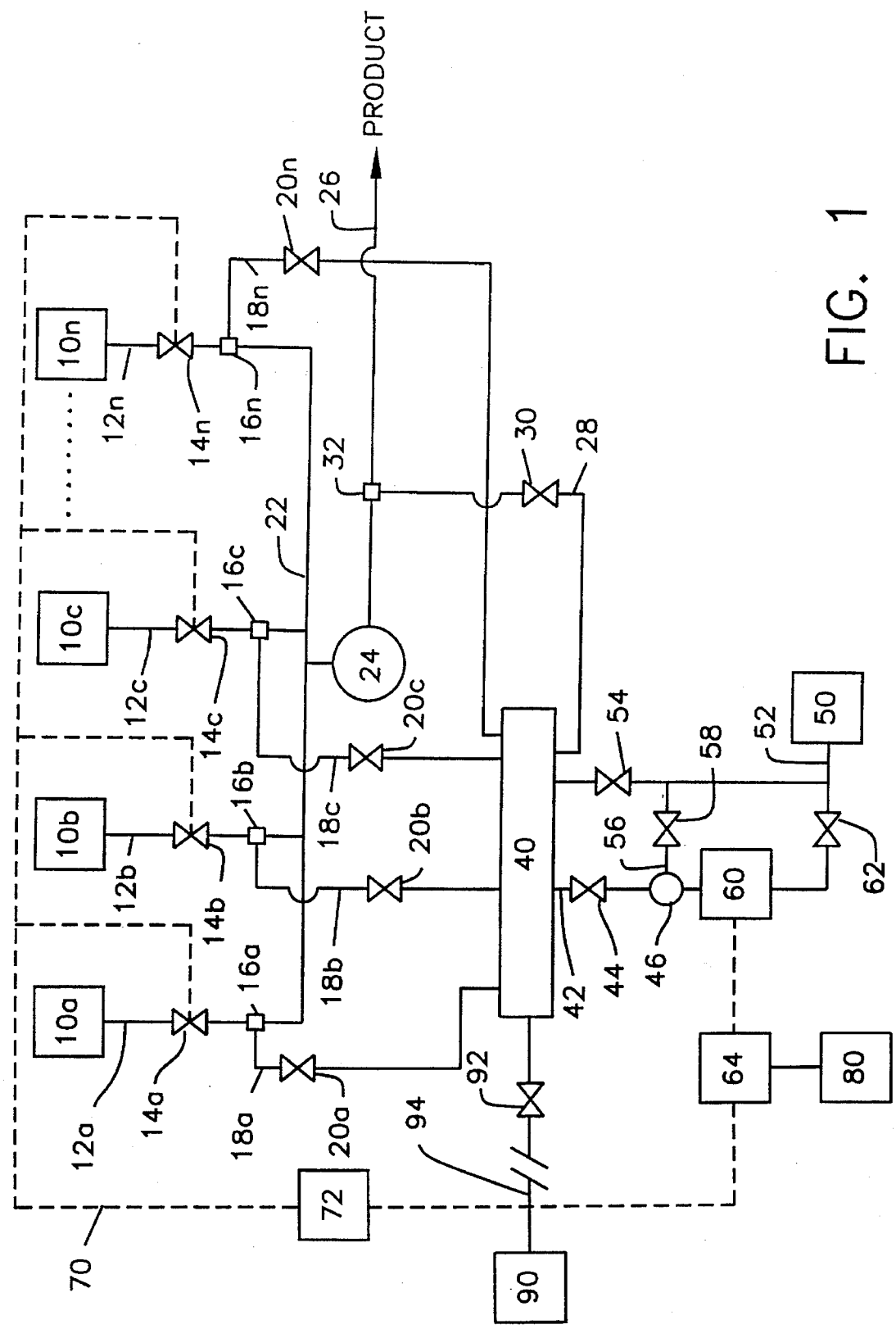
FIG. 1 is a schematic flow diagram of the blend process, control valves, GC/MS analytical center and computer control system.

FIG. 1 is a schematic flow diagram of an on-line blend process. In FIG. 1, blending stocks are contained in Tanks $10a$ to $10n$ where n is the number of blend tanks. Each blend tank is connected to a common gathering line 22 which feeds into a blending or mixing tank 24. The connecting lines $12a$ to $12n$ are interrupted by control valves $14a$ to $14n$ and sampling ports $16n$ a to $16n$. Sampling ports $16a$ to $16n$ are connected to a sampling manifold 40 through lines $18a$ to $18n$ which are interrupted by control valves $20a$ to $20n$. Product line 26 is also connected through sampling port 32 to sampling manifold 40 through line 28 which is interrupted by control valve 30. Sampling manifold 40 is connected to a sample/injection valve 46 by line 42 interrupted by control valve 44. Sampling manifold 40 is also connected to Sump 50 by purge line 52 interrupted by control valve 54. Control valve 46 is also connected to purge line 52 through line 56 interrupted by control valve 58. Sampling manifold 40 and sample/injection 46 are purged by the sample to be analyzed. During the purge phase, sample is collected in sump 50.

Once the sampling manifold 40 and sample/injection valve 46 are purged of any contaminants, sample to be analyzed is injected through valve 46 into GC/MS analyzer 60 which can be purged to sump 50 through valve 62. The raw data generated by GC/MS analyzer 60 is fed to computer 64 where it is subjected to mathematical treatment. Output from computer 64 is fed as an electronic signal through line 70 to blend control computer 72 which electronically controls valves $14a$ to $14n$ thereby controlling product quality exiting blending unit 24.

For at-line operation, sampling manifold 40 is connected to a remote blend stock source 90 through line 94 interrupted by control valve 92. For off-line operation, a remotely collected sample is directly injected into GC/MS analyzer 60 by sample/injection valve 46. Computer output may be read through display panel 80.

The operation of GC/MS analyzer 60 and computer 64 is described in further detail as follows. Blend stocks and blend products are complex hydrocarbon mixtures. The use of GC/MS to analyze such complex mixtures for chemical and physical properties generates a large amount of collinear data. Multiple regression analysis can be used for normal linear data. However, this type of analysis cannot be used for collinear data.

The method according to the invention involves a means for predicting chemical, perceptual, performance and/or physical properties of blend stocks and product blends or refinery or chemical processes by quantitative identification of components using a combination of retention times from a GC analysis coupled with target fragment and/or molecular ions produced by the MS. The MS information is compared against a set of one or more known properties from reference samples which form a training set. By mathematically comparing the experimental data against that of the training set, one may predict the desired property or properties of the blend stock or blend product or refinery or chemical process.

GC/MS utilizes a gas chromatograph interfaced with a mass spectrometer. While a chromatographic method such as supercritical fluid chromatography, liquid chromatography or size exclusion chromatography may be used to separate the mixture into components or mixtures of components, gas chromatography, especially capillary gas chromatography is our preferred means for interfacing with a mass spectrometer. Both GC and MS utilize computer software for instrument control, data acquisition and data reduction. The computer platform should be capable of acquiring at least 2000 mass spectra in about 7 minutes.

The sample mixture to be analyzed is first injected into a GC where the mixture components are separated as a function of retention time, typically on the basis of boiling point. Only partial chromatographic resolution of mixture components is necessary. The GC oven temperature is usually programmed for samples with a wide boiling range. Components may also be identified by a detector such as a flame ionization detector, atomic emission detector, thermal conductivity detector or electron capture detector.

The separated or partially separated components are then introduced into a mass spectrometer under dynamic flow conditions. Since a GC operates under atmospheric pressure and a MS under vacuum conditions (about $10^{-3}$ kPa), the instrument interface requires a coupling device such as a molecular separator (e.g., jet, membrane, etc.), open split coupler or capillary direct interface to efficiently transfer sample while minimizing carrier gas effects.

Depending on the nature of the sample, the mixture may be introduced directly into a MS using a direct insertion probe without a prior GC separation step. Other thermal separation techniques not involving a GC may be used to introduce the sample into the mass spectrometer.

In the MS, sample molecules are bombarded with high energy electrons thereby creating molecular ions which fragment in a pattern characteristic of the molecular species involved. A continuous series of mass spectra are obtained over a scan range of 10 or more daltons to at least 450 daltons. The mass spectral data may also be acquired in the selected ion monitoring (SIM) mode. In the selected ion mode, care must be taken to select ions representative of the components of interest and to operate under repeatable conditions. A variety of MS instruments may be used including low resolution, high resolution, MS/MS (hybrid or triple quadrupole, etc.), ion cyclotron resonance and time of flight. Any ionization technique may be used, such as electron ionization, chemical ionization, multiphoton ionization, field desorption, field ionization, etc., provided that the technique provides either molecular or fragment ions which are suitable for use in the analysis procedure.

The results of sample analysis are a series of 1 mass spectra. The mass spectra are divided into n time intervals where n is an integer from 1 to 1. At least one diagnostic ion is chosen from each of m time intervals where m is an integer from 1 to n. The term "diagnostic ion" refers to an ion which is representative of a compound, a chemical class or a performance, perceptual or physical property correlated thereto. Regardless of whether mass spectra are obtained in the scan or selected ion mode, it is important that the mass spectra be obtained under conditions which will yield diagnostic ions of suitable and repeatable intensity and accuracy.

If the mass spectral data are acquired in the scan mode, the mass range covered during the acquisition should be sufficient to provide acquisition of all of the ions which could be used as diagnostic ions during mathematical treatment in each mass spectral scan. If the mass spectral data are acquired in the selected ion monitoring mode, then care must be taken that the ions selected for monitoring are suitable for use in measuring the components of interest.

The sample mass spectral data are then compared to mass spectral data from a series of reference samples with known performance, perceptual, physical and/or chemical properties. In order to compare reference mass spectral data with sample mass spectral data, it may be desirable to time align the sample data to help ensure the integrity of the comparison. There are commercially available computer programs for such data alignment, for example, Hewlett-Packard GC/MS software G1034C version C.01.05.

The reference mass spectral data, and associated properties data, are arranged in matrix form for mathematical treatment as described below. In the case of chemical composition information, one matrix is formed of reference sample ion intensities at given masses and the other matrix contains known ion intensities for molecular fragment ions of known components. The training set for chemical composition data is thus made up of mass spectral data for different components characteristic of compounds or molecular series expected to be found in the sample mixtures. Similar training sets can be formed for other chemical or perceptual or performance or physical properties of interest. These training sets form one block or matrix of data (Y-block or properties matrix). The actual sample mass spectral data (which may have been time aligned) form the other block (X-block) or matrix of data. These two matrices are subjected to mathematical treatment known as Partial Least Squares (PLS), or Principal Component Regression (PCR), or Ridge Regression (RR) to obtain a mathematically describable relationship between the properties data and mass spectral data, known as a model. Coefficients provided by this model are mathematically combined with the suitably treated mass spectral data from samples with unknown desired properties to:

a) predict desired properties, b) assess the suitability of the model for such predictions, and c) diagnose the stability and general correctness of the process that yielded the mass spectral data PLS/PCR/RR are described in the literature, e.g., Wold S., A. Ruhe, H. Wold, and W. J. Dunn, "The Collinearity Problem in Linear Regression. The Partial Least Squares (PLS) Approach to Generalized Inverses", SIAM J. Sci. Stat. Comput., 1984 5(3), 735–743, or Geladi P., and B. R. Kowalki, "Partial Least Squares Regression: A Tutorial", Anal. Chim. Acta, 1986, 185, 1–17, or Hökuldsson A., "PLS Regression Methods", J. Chemometrics, 1988, 2, 211–228, or in many other articles in journals such as the Journal of Chemometrics or Intelligent Laboratory Systems; Frank, I. and J. Friedman, "A Statistical View Of Some Chemometrics Regression Tools", Technometrics, 1993, Vol. 35, No. 2; Jackson, J. E., "A User's Guide To Principal Components", Wiley-Interscience, New York, 1991; Montgomery, D. C. and E. A. Peck, "Introduction To Linear Regression Analysis", Wiley-Interscience, New York, 1990; and Martens, H., and T. Naes, "Multivariable Calibration", Wiley-Interscience, New York, 1989.

When dealing with a complex mixture, it is necessary to select appropriate masses or groups of masses at specific retention times for a particular compound or classes of compounds. The selection of such masses are the basis for a set of rules which then forms the data for the training set.

There are no set procedures for such a selection process. The researcher must select appropriate masses for compounds of interest. For example, motor gasolines typically contain paraffins, cycloparaffins olefins and aromatics. It is known that paraffinic hydrocarbons yield fragment ions at masses 43, 57, 71, 85, . . . daltons, and these masses may be used as diagnostic of this class of compounds. Moreover, when coupled with retention time data, it is possible to identify concentrations of specific compounds within this class of compounds. In a similar manner, training sets for other chemical, performance, perceptual or physical properties may be developed by correlating compositional data with other properties of interest, e.g., boiling range, viscosity and the like. The result of a mathematical treatment such as PLS/PCR/RR of the training set is a set of coefficients for the properties of interest.

These coefficients are then multiplied by the data matrix for the sample. The result is a prediction of the desired property or properties which can then be used to control the blend process and product quality; or to control various refinery or chemical process operating units depending on the quality of the feed stocks or products. Moreover, variances in properties serve to promptly alert operators of upsets/changes in operating conditions which could influence product quality. The method of the invention is further illustrated by the following examples.

EXAMPLE 1

The method for predicting the physical, perceptual, performance or chemical properties of a complex hydrocarbon mixture such as a blend product or blend stock or refinery or chemical process feed, intermediate or final stream is demonstrated in this example using research octane number (RON) as the specific property for purposes of illustration. The method is generally applicable to a range of other performance properties as well as physical, perceptual or chemical properties of such mixtures.

The initial consideration is to establish a set of standard GC/MS operating parameters so that the GC/MS analytical data used for predicting properties are obtained under consistent operating conditions. The GC/MS instrument used in this example is a Hewlett-Packard 5972 Mass Selective Detector interfaced to a Hewlett-Packard 5890 Series II Gas Chromatograph fitted for use with microbore columns also fitted with a Vortex Cooler for rapid column oven cooling and a liquid sampling valve.

The GC/MS operating conditions are summarized in Table 1.

TABLE 1

| GC Conditions | |
| --- | --- |
| Column | Phenyl Silicone (such as HP-5) 10 m × 0.1 mm, 17 micron film thickness |
| Temperature Program | |
| Initial Temperature (°C.) | 35 |
| Initial Time (minutes) | 3 |
| Program Rate (°C./minute) | 30 |

TABLE 1-continued

| GC Conditions | |
| --- | --- |
| Final Temperature (°C.) | 230 |
| Final Time (minutes) | 1 |
| Injection Valve Temperature (°C.) | 70 |
| Injection Valve On (minutes) | 1.01 |
| Injection Valve Off (minutes) | 1.15 |
| Injection Port Temperature (°C.) | 275 |
| Injection Volume μL | 0.5 |
| Carrier Gas | Helium |
| Linear Velocity | 25.6 |
| Split Ratio | 500:1 |
| Column Head Press, kPa | Approx. 260 |
| Interface Temperature (°C.) | 280 |
| Vortex Cooler | |
| Delivery Air Pressure (psi) | 55 |
| Cooler Off (minutes) | 4.00 |
| Cooler On (minutes) | 10.48 |
| Mass Spectrometer Conditions | |
| Mass Spectrometer On (minutes) | 1.00 |
| Ionization Mode | Electron Ionization 70 eV nominal |
| Mass Range Scanned (daltons) | 10–400 |
| Cycle Time (minutes) | 0.003 |

In order to predict properties of an unknown hydrocarbon mixture, it is first necessary to select reference samples having known values of the property or properties of interest. These reference samples are used to form a training set as described below. Six hundred twenty seven (627) samples comprised the training set for RON. These samples were analyzed under on-line conditions over a 12 month period and covered the range 89.3 to 96.9 RON (ASTM D 2885-90). These samples were chosen from over 26,000 samples acquired during testing over a 14 month period as representing the variation in gasoline blending using 9 different refinery streams and MMT (methycyclopentadienyl manganese tricarbonyl). The 627 samples in the training set were further chosen during periods of stable blending operation at average blend rates of 2230+ barrels/hour.

A data treatment method should be selected prior to obtaining raw GC/MS data. Two types of data treatments which may be used are Chemist's Rules and Hydrocarbon Compound Type Analysis as described, for example, in ASTM D 2789-90 "Test Method for Hydrocarbon Types in Low Olefinic Gasoline by Mass Spectrometry". Chemist's Rules involve two separate sections: (1) a calibration section to correct retention times, i.e., the time between zero and the time when a given peak occurs; and (2) the actual Rules which are based on a selected series of masses corresponding to prominent compounds or molecular series expected for the type of hydrocarbon mixture under investigation. These compounds or compound types are selected on the basis that they have prominent molecular and/or fragment ions unique to that compound or molecular series. A portion of the Chemist's Rules are shown in Table 2. A full set of Chemist's Rules for motor gasoline are shown following Example 6.

TABLE 2

Chemist's Rules for Mogas

| Rule[a] | Compound[b] | Masses[c] | | | | | Retention Time[d] Start | End |
|---|---|---|---|---|---|---|---|---|
| 1 | C3= | 27 | 41 | 42 | | | 1.560 | 1.590 |
| 2 | C3 | 29 | 43 | 44 | | | 1.570 | 1.600 |
| 3 | iC4 | 29 | 43 | 58 | | | 1.605 | 1.624 |
| 4 | nC5 | 29 | 43 | 58 | | | 1.624 | 1.680 |
| 5 | C5= | 27 | 41 | 55 | 70 | | 1.684 | 1.708 |
| 6 | C5 | 29 | 43 | 57 | 72 | | 1.705 | 1.739 |
| 7 | C5= | 27 | 41 | 55 | 70 | | 1.736 | 1.772 |
| 8 | C5 | 29 | 43 | 57 | 72 | | 1.739 | 1.794 |
| 9 | C5= | 27 | 41 | 55 | 70 | | 1.772 | 1.794 |
| 10 | C5/-2 | 39 | 53 | 68 | | | 1.775 | 1.796 |
| 11 | C5= | 27 | 41 | 55 | 70 | | 1.794 | 1.840 |
| 12 | C5/-2 | 39 | 53 | 68 | | | 1.796 | 1.839 |
| 13 | C5/-2 | 39 | 53 | 68 | | | 1.839 | 1.873 |
| 14 | C5/-4 | 39 | 40 | 65 | 66 | | 1.856 | 1.882 |
| 15 | C6= | 27 | 41 | 55 | 56 | 69 84 | 1.907 | 1.934 |
| 16 | C6 | 29 | 43 | 57 | 71 | 86 | 1.926 | 1.973 |
| . | . | . | . | . | . | . | . | . |
| . | . | . | . | . | . | . | . | . |
| 138 | ClBenzothio | 145 | 147 | 148 | | | 7.701 | 7.849 |
| 139 | 2Me/-12 | 141 | 142 | | | | 7.722 | 7.770 |
| 140 | 1Me/-12 | 141 | 142 | | | | 7.820 | 7.861 |
| 141 | C2/-12 | 141 | 156 | | | | 8.283 | 8.382 |
| 142 | Phenanthrene | 178 | | | | | 9.500 | 10.000 |

[a]Rule number, integer index
[b]Compound or group of compounds rule applies to, for example
C3= refers to olefin or cycloparaffin with 3 carbons
C5/-2 refers to diolefin, dicycloparaffin or cyclo-olefin with 5 carbons
C5/-4 refers to triolefin, tricycloparaffin, dicyclo-olefin, cyclodiolefin with a total of 5 carbons
ClBenzothio methyl substituted benzothiophene ($C_nH_{2n-10}S$)
[c]Masses used in Rule [up to n may be specified, where n is an integer which is equal to the number of masses scanned during the time interval (d) either in full scan mode or selected ion monitoring mode].
[d]Retention Time for both starting and ending expected retention times based on historical averages in minutes.

A reference retention time is then determined for each mass spectral ion grouping selected for use in the Chemist's Rules for each of the selected compound types or specific molecules identified in Table 2. Such corrections are necessary due to slight shifts in retention times which may result from column degradation, column head pressure fluctuations, changes in column carrier gas linear velocity, or minor fluctuations in the GC column oven temperatures or other causes. The calibration step generates a series of correction factors for the entire GC/MS data file. The results of applying such corrections are shown in Table 3.

TABLE 3

| Mass (a) | Reference Time (b) | Type (c) | Limit (d) | Calibration Time (e) | Correction (f) |
|---|---|---|---|---|---|
| 58 | 1.652 | P | | 1.642 | -0.010 |
| 78 | 2.556 | P | 0.100 | 2.549 | -0.007 |
| 92 | 3.863 | P | | 3.862 | -0.001 |
| 106 | 4.917 | P | | 4.933 | 0.016 |
| 128 | 7.148 | P | | 7.163 | 0.015 |
| 142 | 7.746 | P | | 7.770 | 0.024 |

(a) Mass or compound selected for the calibration.
(b) Expected occurrence time, typically based on average of several analyses.
(c) P = Peak or maximum occurrence; F = First occurrence of the material
(d) Range (± minutes) for reference compound
(e) Observed retention time for reference material
(f) Correction to be applied between reference materials (column a). Correction for the first material is from initial time to calibration time; correction for the second material is between first and second reference materials; and the last correction is applied to end of data acquisition.

Once the correction coefficients are determined, the actual Rules are then determined. In the case of research octane number prediction, a total of 142 Rules is used based on compound or compound series identifications. For each Rule, a set of characteristic mass numbers is determined. These characteristic mass numbers can range from 1 to n, where n is an integer representing the entire mass range scanned or the number of selected ions being monitored. In this case, up to seven characteristic mass numbers are illustrated. The ion intensities of the masses for each Rule are summed within the upper and lower retention time limits for that Rule. The results are shown for a sampling of the 142 Rules in Table 4 for this demonstration analysis. Table 4 is shown in its entirely following Example 6.

TABLE 4

CHEMIST'S RULES FOR MOGAS WITH CORRECTIONS

| | | | | | | |
|---|---|---|---|---|---|---|
| Total Raw Abundance (TIC): | 125963855 | | |
| Chemist Rule: | 80972353 | (64.282%) | |
| Air Leakage: | 7201540 | (5.717%) | |
| Avg Scan Rate (Min/Max): | 128 | (126/215) | |
| Number of Records: | 4857 | | |

| Rule[a] | Compound[b] | Masses[c] | | | | | Start[d] | End[e] | CStart[f] | Corr[g] | CEnd[h] | Corr[i] | Abundance[j] | |
|---|---|---|---|---|---|---|---|---|---|---|---|---|---|---|
| 1 | C3= | 27 | 41 | 42 | | | 1.560 | 1.590 | 1.551 | −0.009 | 1.581 | −0.009 | 0 | 0.00% |
| 2 | C3 | 29 | 43 | 44 | | | 1.570 | 1.600 | 1.561 | −0.009 | 1.591 | −0.009 | 0 | 0.00% |
| 3 | iC4 | 29 | 43 | 58 | | | 1.605 | 1.624 | 1.596 | −0.009 | 1.614 | −0.010 | 14233 | 0.02% |
| 4 | nC5 | 29 | 43 | 58 | | | 1.624 | 1.680 | 1.614 | −0.010 | 1.670 | −0.010 | 715655 | 0.88% |
| 5 | C5= | 27 | 41 | 55 | 70 | | 1.684 | 1.708 | 1.674 | −0.010 | 1.698 | −0.010 | 20805 | 0.03% |
| 6 | C5 | 29 | 43 | 57 | 72 | | 1.705 | 1.739 | 1.695 | −0.010 | 1.730 | −0.009 | 1129596 | 1.40% |
| 7 | C5= | 27 | 41 | 55 | 70 | | 1.736 | 1.772 | 1.727 | −0.009 | 1.763 | −0.009 | 780267 | 0.96% |
| 8 | C5 | 29 | 43 | 57 | 72 | | 1.739 | 1.794 | 1.730 | −0.009 | 1.785 | −0.009 | 1189151 | 1.47% |
| 9 | C5= | 27 | 41 | 55 | 70 | | 1.772 | 1.794 | 1.763 | −0.009 | 1.785 | −0.009 | 1097894 | 1.36% |
| 10 | C5/-2 | 39 | 53 | 68 | | | 1.775 | 1.796 | 1.766 | −0.009 | 1.787 | −0.009 | 194465 | 0.24% |
| 11 | C5= | 27 | 41 | 55 | 70 | | 1.794 | 1.840 | 1.785 | −0.009 | 1.831 | −0.009 | 1219014 | 1.51% |
| 12 | C5/-2 | 39 | 53 | 68 | | | 1.796 | 1.839 | 1.787 | −0.009 | 1.830 | −0.009 | 213325 | 0.26% |
| 13 | C5/-2 | 39 | 53 | 68 | | | 1.839 | 1.873 | 1.830 | −0.009 | 1.864 | −0.009 | 48362 | 0.06% |
| 14 | C5/-4 | 39 | 40 | 65 | 66 | | 1.856 | 1.882 | 1.847 | −0.009 | 1.873 | −0.009 | 35019 | 0.04% |
| 15 | C6= | 27 | 41 | 55 | 56 | 69 84 | 1.907 | 1.934 | 1.898 | −0.009 | 1.925 | −0.009 | 47825 | 0.06% |
| 16 | C6 | 29 | 43 | 57 | 71 | 86 | 1.926 | 1.973 | 1.917 | −0.009 | 1.964 | −0.009 | 1586920 | 1.96% |
| . | . | . | . | . | . | . | . | . | . | . | . | . | . | . |
| 138 | C1Benzothio | 145 | 147 | 148 | | | 7.701 | 7.849 | 7.724 | 0.023 | 7.873 | 0.024 | 255718 | 0.32% |
| 139 | 2MeNaphthalene | 141 | 142 | | | | 7.722 | 7.770 | 7.746 | 0.024 | 7.794 | 0.024 | 1030117 | 1.27% |
| 140 | 1MeNaphthalene | 141 | 142 | | | | 7.820 | 7.861 | 7.844 | 0.024 | 7.885 | 0.024 | 410403 | 0.51% |
| 141 | C2 Naphthalene | 141 | 156 | | | | 8.283 | 8.382 | 8.307 | 0.024 | 8.406 | 0.024 | 39022 | 0.05% |
| 142 | Phenanthrene | 178 | | | | | 9.500 | 10.00 | 9.524 | 0.024 | 10.024 | 0.024 | 0 | 0.00% |
| | Sum = | | | | | | | | | | | | 80972353 | 100.00% |

[a]Rule number, integer index
[b]Compound or group of compounds rule applies to, for example
C3= refers to olefin or cycloparaffin with 3 carbons
C5/-2 refers to diolefin, dicycloparaffin or cyclo-olefin with 5 carbons
C5/-4 refers to triolefin, tricycloparaffin, dicyclo-olefin, cyclodiolefin with a total of 5 carbons
C1Benzothiophene methyl substituted benzothiophene ($C_n/H_{2n-10}S$)
[c]Masses used in Rule [up to n may be specified, where n is an integer which is equal to the number of masses scanned during the time interval (d to e) either in full scan mode or selected ion monitoring mode].
[d]start retention time in minutes
[e]end retention time in minutes
[f]corrected start retention time, in minutes
[g]correction = difference between start and cstart (in minutes)
[h]corrected end time, in minutes
[i]correction = difference between end and cend (in minutes)
[j]Abundance, both as total sum and as normalized percentage based on Chemist's Rules.
Total Raw Abundance (TIC): total area observed in the GC/MS analysis.
Chemist Rule: total area found using the Chemist's Rules; based on experience, should be greater than 30% of total raw abundance.
Air Leakage: total ionization due to air (m/z 28, 32, 44, 44) useful diagnostic for instrumentation difficulties.
Average Scan Rate (Min/Max): shows the minimum, average and maximum scan rates during the GC/MS analysis and is a useful diagnostic to identify instrumental problems.
Number of records: is the number of mass spectral scans acquired during the analysis.

The analysis summarized in Table 4 is done for each reference sample. The results from these respective analyses form a training set which is subjected to mathematical treatment. The goal is to develop a model that can be use to predict the unknown properties of future samples using their mass spectral data only. The mathematical treatments are described by multivariate correlation techniques such as Projection to Latent Structures (PLS) or otherwise known as Partial Least Squares (PLS), Principal Component Regression (PCR), and Ridge Regression (RR). These techniques are superior to ordinary multiple linear regression in their ability to treat collinearity amongst variables in the X-block or GC/MS data matrix (and Y-block or properties matrix for PLS), and in their ability to handle the quantity of data generated by the Chemist's Rules. Ordinary Multiple Linear Regression cannot be used to treat collinear variables.

PLS/PCR/RR are numerical analysis techniques for detecting and formulating a mathematical structure (model) within a data set comprising observations associated with multiple objects. Each object has associated with it observations for multiple variables, the latter being common to all objects. These multiple variables are assigned into two categories, known as X-block and Y-block. Observations associated with all variables in the X-block are realized from a common process (GC/MS data in this case). Observations associated with variables in the Y-block (known properties in this case) are realized from processes that may be different for each variable. The data set used to construct this mathematical model is referred to as the model calibration data set.

The common use of PLS/PCR/RR is to apply the model developed from the calibration data set to X-block observations realized for new objects (not in the calibration dataset) to predict values for the corresponding variables in the Y-block for these new objects, without having to execute the Y-block processes used in the calibration dataset. Using diagnostics that are simultaneously generated by the PLS/PCR/RR model, assessment of whether the new objects can be adequately described by the model, and whether the model is used in an extrapolation mode versus interpolation mode can be performed.

PLS/PCR addresses the collinearity features in the X-block and Y-block, by suitably reducing the dimensionally in both X and Y blocks (for PLS), and X-block only (for PCR) to form the model. Collinearity is a term referring to the existence of relationships between variables within the block itself. In the PLS modeling algorithm a number of independent dimensions in the X- and Y-blocks are identified by forming pseudo-variables known as principal components or latent vectors through different sets of linear combinations of original variables in each block. Each set of such combinations constitutes an independent dimension. It comprises a set of coefficients that each value associated with each variable in the block is to be weighted by to arrive at the new value for this dimension. The values for the new, reduced dimensions in the Y-block are regressed onto their counterparts in the new, reduced dimensions of the X-block to arrive at the most parsimonious dimension size (number of latent vectors) and their associated weights, with the final goal of one linear equation generated to permit prediction of Y-block variables using X-block variables. The number of dimensions used to construct the model is determined through optimization of a criterion known as PRESS (Prediction Error Sum of Squares), cumulated by a Cross Validation (CV) technique using the training data set, and, following the general model parsimony principle.

For PCR, the number of independent dimensions in the X-block are first selected and identified in a similar fashion as in PLS by forming principal components. Then, for each variable in the Y-block, a model is obtained by performing ordinary multiple linear regression using the Principal Components as "Prediction Variables".

For Ridge Regression, the collinearity problem is dealt with in a different manner than PLS/PCR. Here a diagonal matrix known as the Lambda Matrix is added to the Covariance Matrix of the X-block with the net effect of stabilizing the numerical computation needed to obtain the model coefficients. The selection of Lambda values is through optimization of PRESS criterion using cross validation of the training set.

Thus, the Chemist's Rule data for the various reference samples derived from GC/MS analysis form the X-block variables. PLS/PCR/RR treatment may require preliminary reorganization of the X-block data, such as transposition and removal of redundant data and constants or mathematical transformations. The Y-block variables are the property (or properties) to be predicted, and may also require mathematical transformations such as logarithmic or geometric, as well as reorganization. The data blocks may be represented by:

X-BLOCK MATRIX
[ Chemist's Rules ($n$ samples $\times$ 142 columns) ]

$$\begin{vmatrix} X_{1,1} & X_{1,2} & X_{1,3} & \ldots & X_{1,140} & X_{1,141} & X_{1,142} \\ X_{2,1} & X_{2,2} & X_{2,3} & \ldots & X_{2,140} & X_{2,141} & X_{2,142} \\ X_{3,1} & X_{3,2} & X_{3,3} & \ldots & X_{3,140} & X_{3,141} & X_{3,142} \\ \cdot & \cdot & \cdot & \cdot & \cdot & \cdot & \cdot \\ \cdot & \cdot & \cdot & \cdot & \cdot & \cdot & \cdot \\ \cdot & \cdot & \cdot & \cdot & \cdot & \cdot & \cdot \\ X_{n,1} & X_{n,2} & X_{n,3} & \ldots & X_{n,140} & X_{n,141} & X_{n,142} \end{vmatrix}$$

Y-BLOCK VECTOR
[ Measured Property or Properties ($n$ samples) ]

$$\begin{vmatrix} Y_1 \\ Y_2 \\ Y_3 \\ \cdot \\ \cdot \\ \cdot \\ Y_n \end{vmatrix}$$

The Y-block may be a single observation per set of Chemist's Rules as shown above, or it may be a $n \times m$ matrix of observations where there are m different properties to be predicted.

Figure 2:
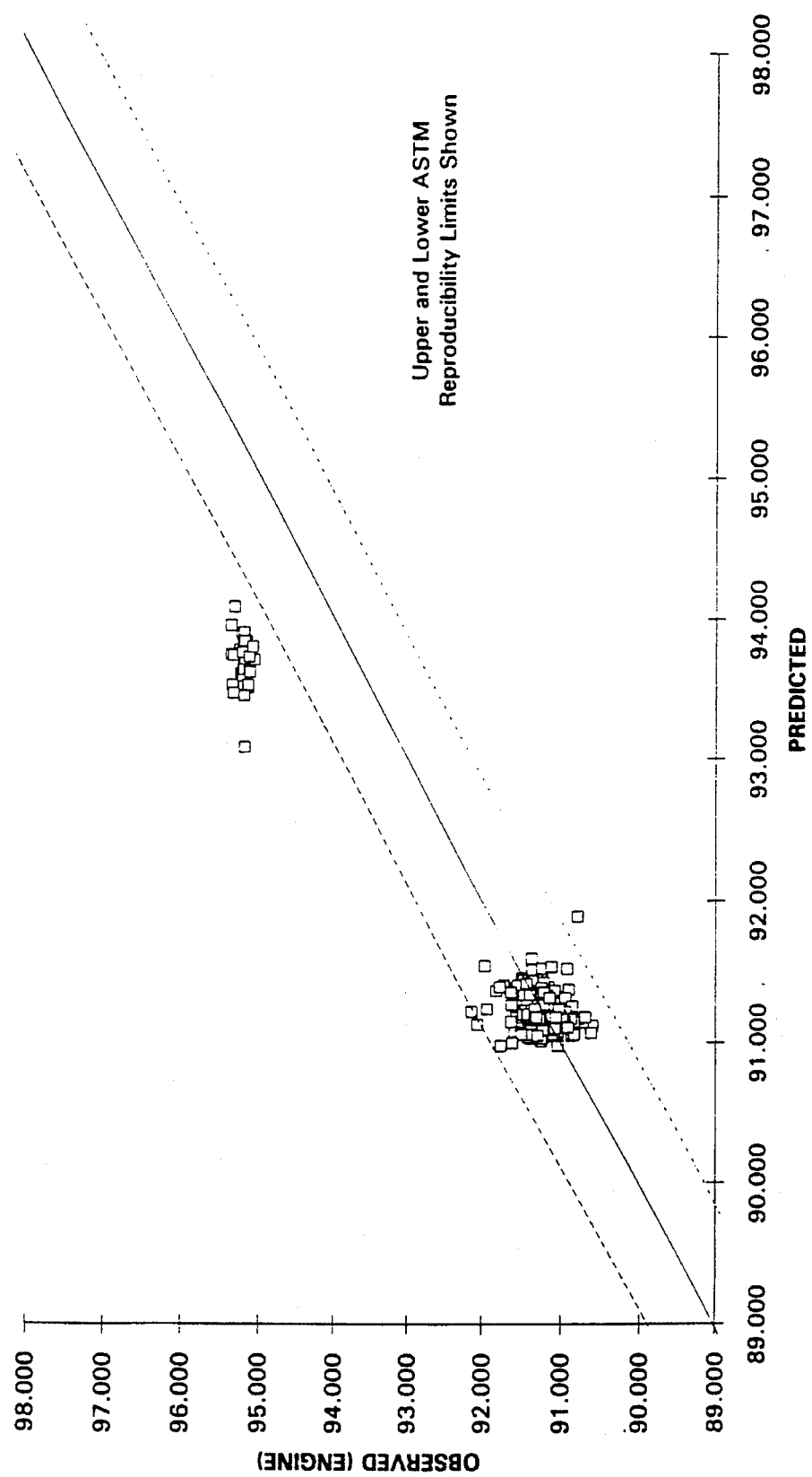
FIG. 2 is a graph showing predicted versus measured research octane values for the training set.
Figure 3:
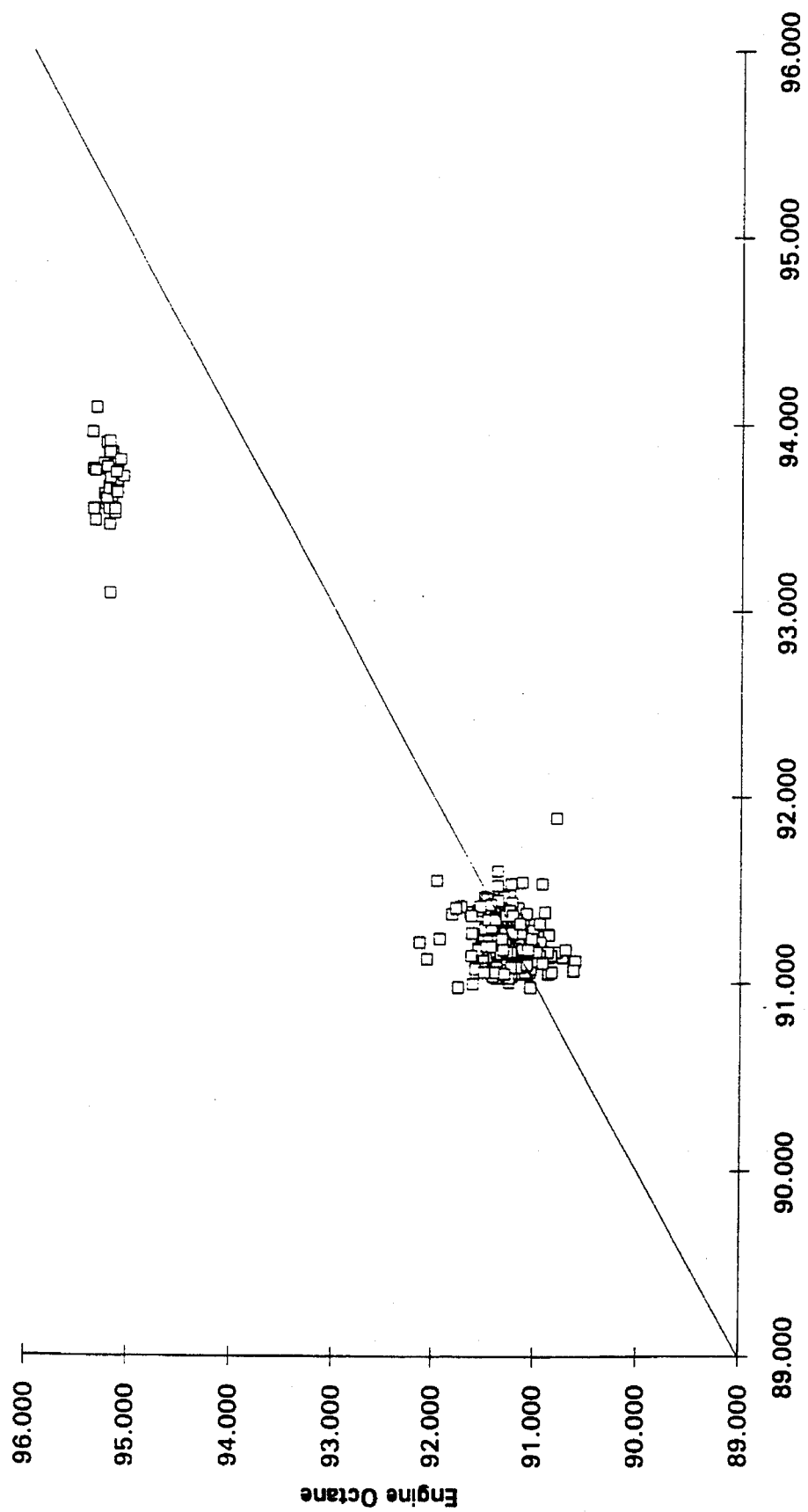
FIG. 3 is a graph showing predicted versus measured research octane values for the test set.

The results of PLS/PCR/RR treatment of the training set data are a series of coefficients. Raw GC/MS data from an unknown sample (or samples) are then treated by the Chemist's Rules first to correct the retention times and then to form the ion summations. Each value for the Chemist's Rule ion summation result is then multiplied by the training set coefficients and summed to generate the prediction of the desired property. This is shown in FIG. 2 which is graph of predicted vs. measured RON values for the training set. FIG. 3 is a graph showing predicted vs. measured RON values for the test set. FIGS. 2 and 3 illustrate the quality of the predicted research octane values for both an unknown test set of 500 samples acquired on-line on a motor gasoline blender referenced to the on-line research octane engine (ASTM D 2885-90). The error in the predicted RON values verses the on-line engine values is due to the sparse number of Premium unleaded gasoline blends in the training set. The predicted vs. measured values for regular unleaded gasoline are mostly within ±0.5 RON units.

EXAMPLE 2

Figure 4:
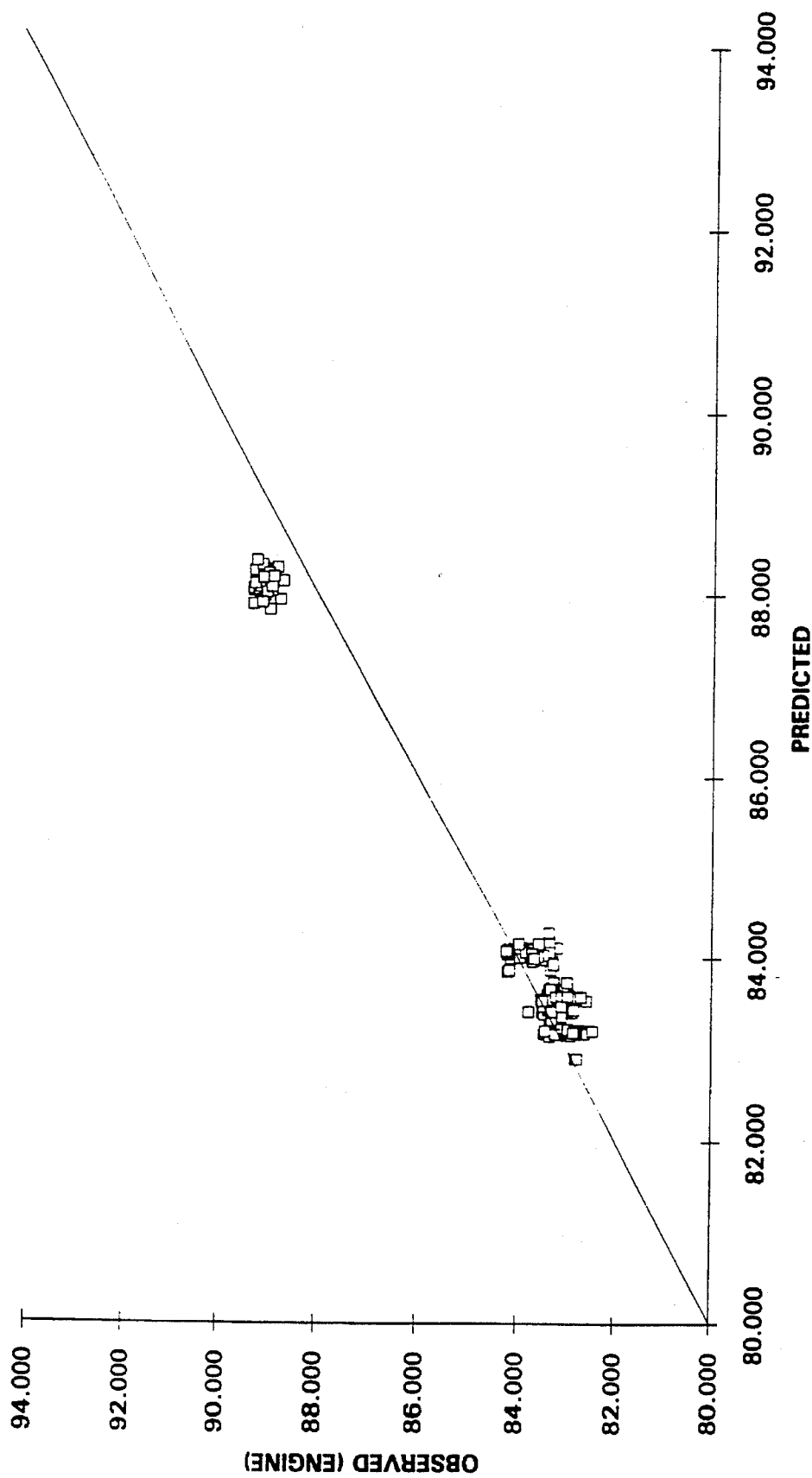
FIG. 4 is a graph showing predicted versus measured motor octane values for the training set.
Figure 5:
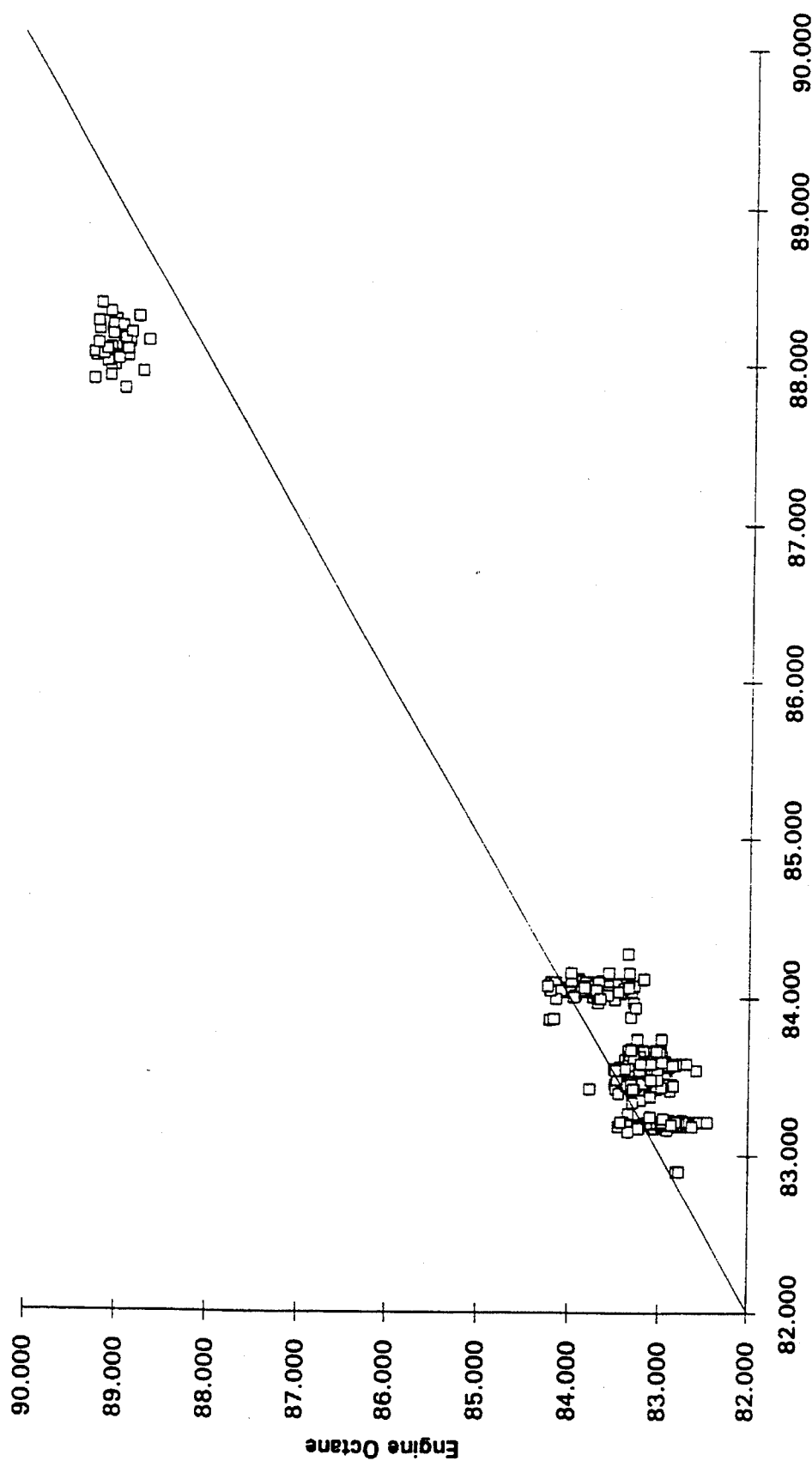
FIG. 5 is a graph showing predicted versus measured motor octane values for the test set.

The procedure of Example 1 was repeated for predicting motor octane number (MON) for motor gasoline. The same 627 member training set was used, with the Y-block values from an on-line MON engine. The same suite of on-line unknown samples were used in the prediction of motor octane number. FIG. 4 is a graph of predicted vs. measured MON values for the training set. FIG. 5 is a graph of predicted and measured MON values for an unknown training set of 500 samples acquired on-line on a motor gasoline blender referenced to the on-line motor octane engine (ASTM D 2855-90). The error in the predicted MON values verses the on-line engine values at high MON values is due to the sparse number of premium unleaded samples in the training set. This error can be offset by a bias correction (of approximately 1.5 octane units) when used for blending control. The predicted vs. measured values for regular unleaded gasoline are mostly within ±MON units.

EXAMPLE 3

Figure 6:
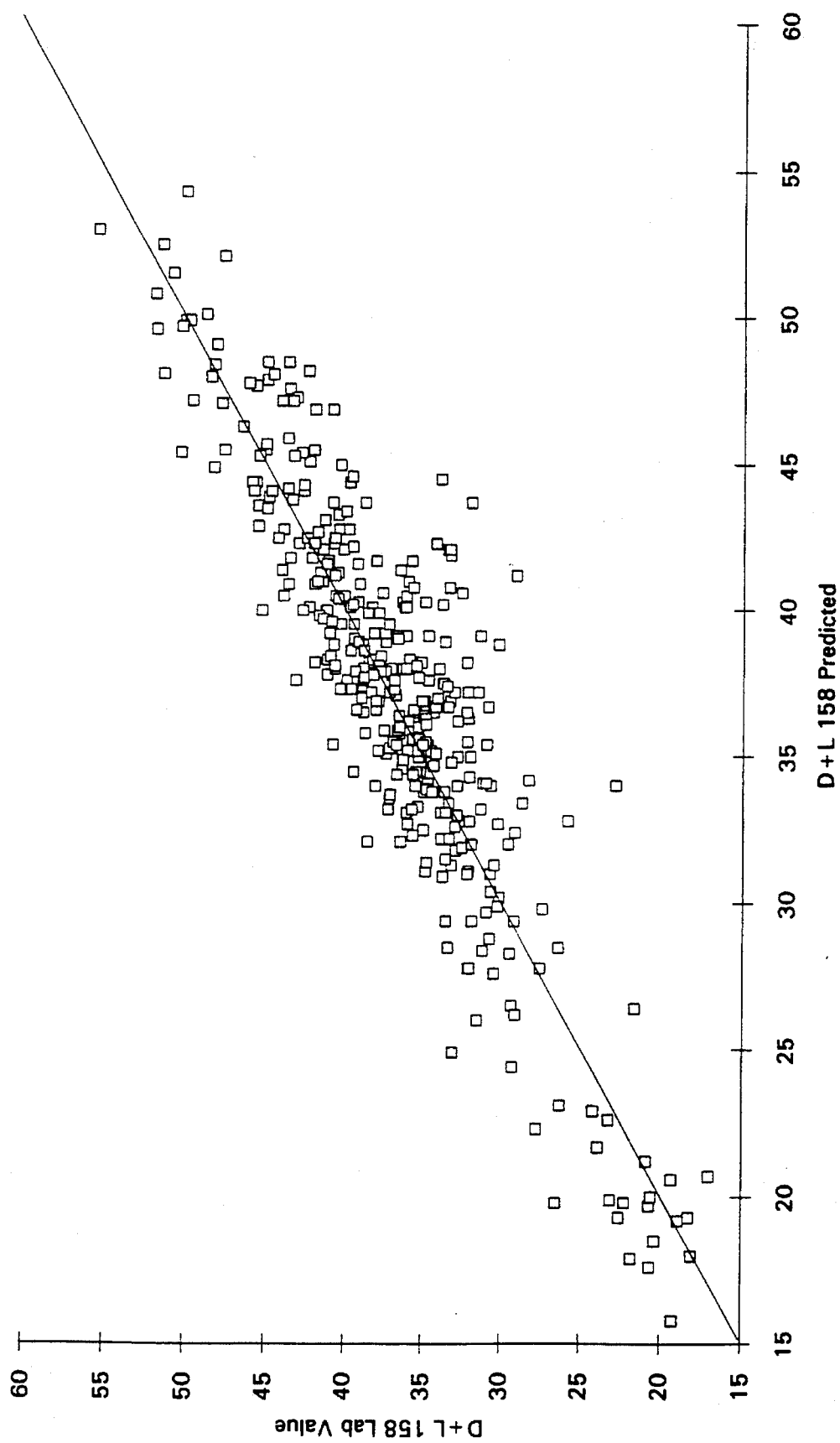
FIG. 6 is a graph showing predicted versus measured D&L values at 158° F. (70° C.) for the training set.

The procedure of Example 1 was repeated for predicting distillation+losses (D+L) at 158° F. (70° C.) for motor gasoline blends. In this example, a training set of 259 members was used with the Y-block data being the laboratory inspection data on once per blend samples. The data ranged from 15.8% to 51.5% with an average value of 36.9%, the samples were analyzed in accordance with ASTM D 86-90. The results for the model training set parity plot are in FIG. 6 which is a graph of predicted vs. measured D+L at 158° F.

EXAMPLE 4

Figure 7:
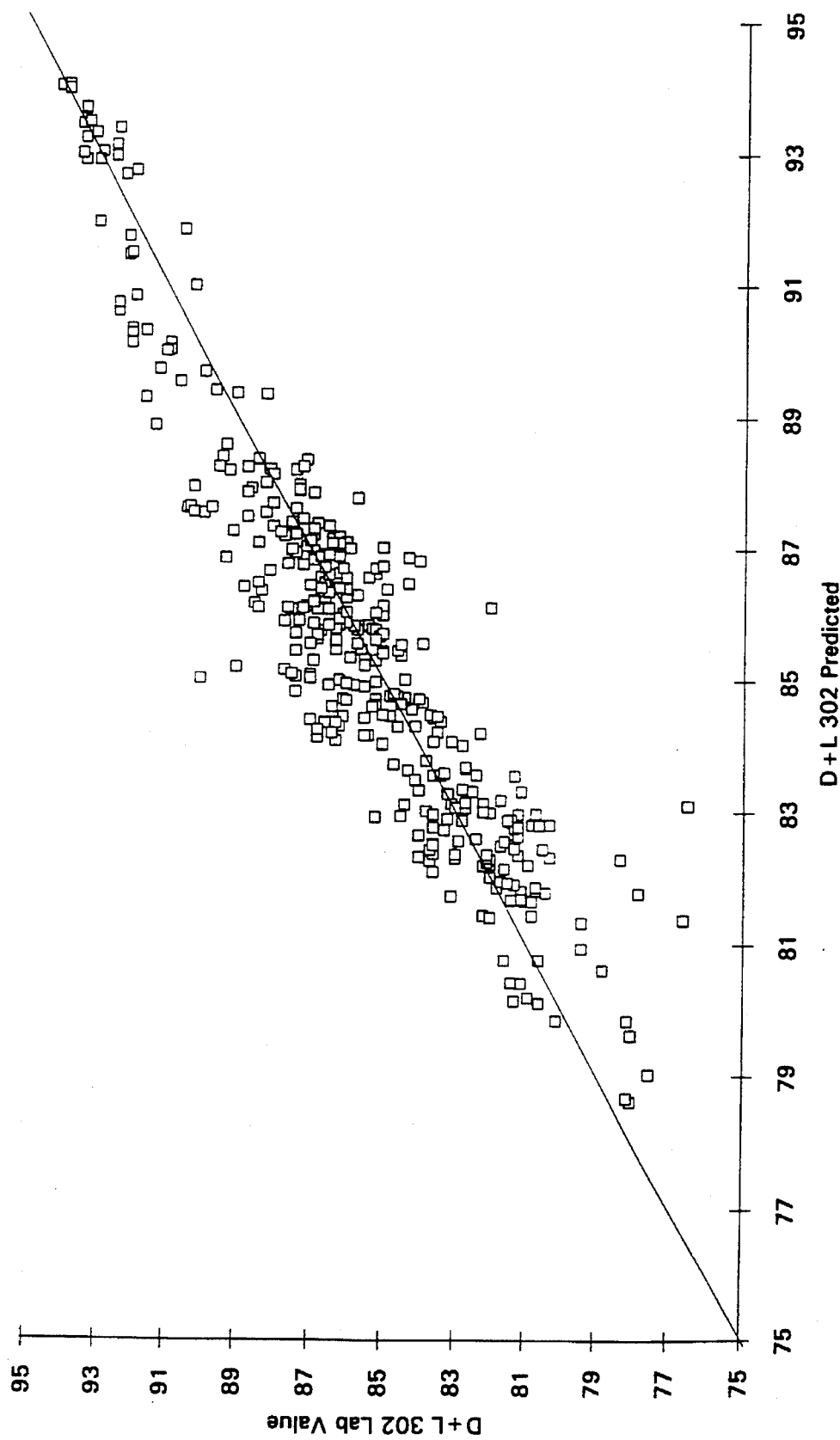
FIG. 7 is a graph showing predicted versus measured D&L values at 302° F. (150° C.) for the training set.

The procedure of Example 1 was repeated for predicting distillation+losses (D+L) at 302° F. (150° C.) for motor gasoline blends. In this example, a training set of 259 members was used with the Y-block data being the laboratory inspection data on once per blend samples. The data ranged from 77.5% to 94.1% with an average value of 85.7%, the samples were analyzed in accordance with ASTM D 86–90. The results for the model training set parity plot are in FIG. 7 which is a graph of predicted vs. measured D+L at 302° F.

EXAMPLE 5

The procedure of Example 1 was repeated for predicting distillation temperature at the 50% distilled point (T50) for motor gasoline blends. In this example, a training set of 261 members was used with the Y-block data being the laboratory inspection data (ASTM D 86-90) on once per blend samples. The data ranged from 153.8 to 236.3° F. (66.7° to 113.5° C.) with an average value of 191.0° F. (88.3° C.). The results for the training set are shown in FIG. 8.

EXAMPLE 6

The procedure of Example 1 was repeated for predicting distillation temperature for 90% distilled point (T90) for motor gasoline blends. In this example, a training set of 261 members was used with the Y-block data being the laboratory inspection data (ASTM D 86-90) on once per blend samples. The data ranged from 263.5 to 349.7° F. (128.6° to 176.5° C.) with an average value of 319.6° F. (159.8° C.). The results for the model training set are shown in FIG. 9 which is a graph of predicted vs. measured T90 in ° F.

Other properties of motor gasoline blends such as upper and lower explosive limits, vapor pressure, flash point, viscosity, heat content, total aromatics (or aromatics by species), reformulated gasoline qualities, etc., could be predicted using the method according to the invention. The subject method can also be applied for predicting properties of other types of complex hydrocarbon mixtures such as diesel fuel, jet fuel, kerosene, heating oil, reformate, alkylate, specialty solvents, etc.; as well as refinery or chemical process feed stocks, intermediate streams and products.

There are several components of blended gasoline which can be measured directly on-line using instrumentation such as described in this patent. These materials include, but are not limited to, water, hydrogen sulfide, benzene, toluene, the isomeric C2 benzenes through C7 benzenes, substituted and unsubstituted indans, styrenes, napthalenes and heavier aromatics or partially hydrogenated aromatics, and various hydrocarbon or oxygenated compound types across the entire carbon number range common to gasolines and/or other materials boiling below 350° C.

| | | Complete Chemist's Rules for Mogas | | | | | | |
|---|---|---|---|---|---|---|---|---|
| | | | | | | | Retention Time[d] | |
| Rule[a] | Compound[b] | | Masses[c] | | | | Start | End |
| 1 | C3= | 27 | 41 | 42 | | | | 1.59 |
| 2 | C3 | 29 | 43 | 44 | | | 1.570 | 1.600 |
| 3 | iC4 | 29 | 43 | 58 | | | 1.605 | 1.624 |
| 4 | nC5 | 29 | 43 | 58 | | | 1.624 | 1.680 |
| 5 | C5= | 27 | 41 | 55 | 70 | | 1.684 | 1.708 |
| 6 | C5 | 29 | 43 | 57 | 72 | | 1.705 | 1.739 |
| 7 | C5= | 27 | 41 | 55 | 70 | | 1.736 | 1.772 |
| 8 | C5 | 29 | 43 | 57 | 72 | | 1.739 | 1.794 |
| 9 | C5= | 27 | 41 | 55 | 70 | | 1.772 | 1.794 |
| 10 | C5/-2 | 39 | 53 | 68 | | | 1.775 | 1.796 |
| 11 | C5= | 27 | 41 | 55 | 70 | | 1.794 | 1.840 |
| 12 | C5/-2 | 39 | 53 | 68 | | | 1.796 | 1.839 |
| 13 | C5/-2 | 39 | 53 | 68 | | | 1.839 | 1.873 |
| 14 | C5/-4 | 39 | 40 | 65 | 66 | | 1.856 | 1.882 |
| 15 | C6= | 27 | 41 | 55 | 56 | 69 | 84 | 1.907 | 1.934 |
| 16 | C6 | 29 | 43 | 57 | 71 | 86 | | 1.926 | 1.973 |
| 17 | C6= | 27 | 41 | 55 | 56 | 69 | 84 | 1.934 | 1.962 |
| 18 | C5= | 27 | 41 | 55 | 70 | | | 1.945 | 1.969 |
| 19 | C6= | 27 | 41 | 55 | 56 | 69 | 84 | 1.962 | 1.982 |
| 20 | C6 | 29 | 43 | 57 | 71 | 86 | | 1.998 | 2.032 |
| 21 | C6= | 27 | 41 | 55 | 56 | 69 | 84 | 2.036 | 2.066 |
| 22 | C6 | 29 | 43 | 57 | 71 | 86 | | 2.076 | 2.117 |
| 23 | C6= | 27 | 41 | 55 | 56 | 69 | 84 | 2.095 | 2.137 |
| 24 | C6= | 27 | 41 | 55 | 56 | 69 | 84 | 2.137 | 2.156 |
| 25 | C6= | 27 | 41 | 55 | 56 | 69 | 84 | 2.156 | 2.178 |
| 26 | C6/-2 | 41 | 53 | 67 | 82 | | | 2.159 | 2.186 |
| 27 | C6= | 27 | 41 | 55 | 56 | 69 | 84 | 2.178 | 2.203 |
| 28 | C6/-2 | 41 | 53 | 67 | 82 | | | 2.186 | 2.204 |
| 29 | C6= | 27 | 41 | 55 | 56 | 69 | 84 | 2.203 | 2.244 |
| 30 | C6= | 27 | 41 | 55 | 56 | 69 | 84 | 2.244 | 2.290 |

-continued

Complete Chemist's Rules for Mogas

| Rule[a] | Compound[b] | Masses[c] | | | | | | Retention Time[d] | |
|---|---|---|---|---|---|---|---|---|---|
| | | | | | | | | Start | End |
| 31 | C7 | 43 | 57 | 71 | 85 | 100 | | 2.252 | 2.276 |
| 32 | C6= | 27 | 41 | 55 | 56 | 69 | 84 | 2.290 | 2.314 |
| 33 | C6/-4 | 39 | 41 | 56 | 79 | 80 | | 2.357 | 2.384 |
| 34 | C6/-4 | 39 | 41 | 56 | 79 | 80 | | 2.384 | 2.415 |
| 35 | C6/-2 | 41 | 53 | 67 | 82 | | | 2.441 | 2.477 |
| 36 | C7= | 41 | 55 | 69 | 70 | 83 | 98 | 2.467 | 2.487 |
| 37 | C7= | 41 | 55 | 69 | 70 | 83 | 98 | 2.519 | 2.537 |
| 38 | Benzene | 78 | | | | | | 2.521 | 2.590 |
| 39 | C6= | 27 | 41 | 55 | 56 | 69 | 84 | 2.524 | 2.562 |
| 40 | C7 | 43 | 57 | 71 | 85 | 100 | | 2.554 | 2.611 |
| 41 | C7= | 41 | 55 | 69 | 70 | 83 | 98 | 2.571 | 2.610 |
| 42 | C7 | 43 | 57 | 71 | 85 | 100 | | 2.645 | 2.684 |
| 43 | C8 | 39 | 41 | 56 | 83 | 99 | 114 | 2.740 | 2.870 |
| 44 | C7= | 41 | 55 | 69 | 70 | 83 | 98 | 2.742 | 2.868 |
| 45 | C7 | 43 | 57 | 71 | 85 | 100 | | 2.771 | 2.793 |
| 46 | C7= | 41 | 55 | 69 | 70 | 83 | 98 | 2.911 | 3.141 |
| 47 | C7 | 43 | 57 | 71 | 85 | 100 | | 2.928 | 2.976 |
| 48 | C7/-2 | 39 | 53 | 67 | 81 | 96 | | 2.978 | 3.025 |
| 49 | C7/-2 | 39 | 53 | 67 | 81 | 96 | | 3.137 | 3.167 |
| 50 | C7= | 41 | 55 | 69 | 70 | 83 | 98 | 3.168 | 3.198 |
| 51 | C7= | 41 | 55 | 69 | 70 | 83 | 98 | 3.246 | 3.300 |
| 52 | C8 | 43 | 57 | 71 | 85 | 99 | 114 | 3.351 | 3.446 |
| 53 | C8 | 43 | 57 | 71 | 85 | 99 | 114 | 3.369 | 3.422 |
| 54 | C8= | 41 | 55 | 69 | 83 | 97 | 112 | 3.371 | 3.396 |
| 55 | C7= | 41 | 55 | 69 | 70 | 83 | 98 | 3.409 | 3.437 |
| 56 | C8= | 41 | 55 | 69 | 83 | 97 | 112 | 3.487 | 3.509 |
| 57 | C7/-2 | 39 | 53 | 67 | 81 | 96 | | 3.488 | 3.508 |
| 58 | C7/-4 | 41 | 56 | 79 | 93 | 94 | | 3.530 | 3.550 |
| 59 | C8= | 41 | 55 | 69 | 83 | 97 | 112 | 3.582 | 3.605 |
| 60 | C8 | 43 | 55 | 57 | 71 | 99 | 114 | 3.585 | 3.661 |
| 61 | C7/-4 | 41 | 56 | 79 | 93 | 94 | | 3.590 | 3.710 |
| 62 | C8 | 43 | 57 | 71 | 85 | 99 | 114 | 3.610 | 3.622 |
| 63 | C8 | 43 | 57 | 70 | 71 | 85 | 99 114 | 3.661 | 3.721 |
| 64 | C7/-2 | 39 | 53 | 67 | 81 | 96 | | 3.676 | 3.727 |
| 65 | C8 | 43 | 57 | 71 | 85 | 99 | 114 | 3.734 | 3.791 |
| 66 | C8= | 41 | 55 | 69 | 83 | 97 | 112 | 3.789 | 3.817 |
| 67 | C8 | 43 | 57 | 71 | 85 | 99 | 114 | 3.805 | 3.940 |
| 68 | Toluene | 91 | 92 | | | | | 3.810 | 3.915 |
| 69 | C7/-2 | 39 | 53 | 67 | 81 | 96 | | 3.874 | 3.899 |
| 70 | C8= | 41 | 55 | 69 | 83 | 97 | 112 | 3.912 | 3.990 |
| 71 | C8= | 41 | 55 | 69 | 83 | 97 | 112 | 4.062 | 4.318 |
| 72 | C8/-2 | 39 | 53 | 67 | 81 | 95 | 110 | 4.167 | 4.181 |
| 73 | C8 | 43 | 57 | 71 | 85 | 99 | 114 | 4.191 | 4.221 |
| 74 | C8/-2 | 39 | 53 | 67 | 81 | 95 | 110 | 4.299 | 4.325 |
| 75 | C8= | 41 | 55 | 69 | 83 | 97 | 112 | 4.491 | 4.559 |
| 76 | C9= | 41 | 69 | 83 | 97 | 111 | 126 | 4.492 | 4.588 |
| 77 | C9 | 43 | 71 | 85 | 99 | 113 | 128 | 4.492 | 4.508 |
| 78 | C9 | 43 | 71 | 85 | 99 | 113 | 128 | 4.556 | 4.578 |
| 79 | C8/-2 | 39 | 53 | 67 | 81 | 95 | 110 | 4.590 | 4.605 |
| 80 | C9= | 41 | 69 | 83 | 97 | 111 | 126 | 4.645 | 4.936 |
| 81 | Et Benzene | 91 | 105 | 106 | | | | 4.804 | 4.856 |
| 82 | C9 | 43 | 71 | 85 | 99 | 113 | 128 | 4.836 | 4.870 |
| 83 | m + p-Xylene | 91 | 105 | 106 | | | | 4.877 | 4.956 |
| 84 | C9 | 43 | 71 | 85 | 99 | 113 | 128 | 4.906 | 4.925 |
| 85 | C9= | 41 | 69 | 83 | 97 | 111 | 126 | 4.972 | 5.084 |
| 86 | o-Xylene | 91 | 105 | 106 | | | | 5.086 | 5.146 |
| 87 | C9= | 41 | 69 | 83 | 97 | 111 | 126 | 5.113 | 5.161 |
| 88 | C9 | 43 | 71 | 85 | 99 | 113 | 128 | 5.138 | 5.159 |
| 89 | C9= | 41 | 69 | 83 | 97 | 111 | 126 | 5.211 | 5.459 |
| 90 | C3 Benzene | 91 | 92 | 105 | 119 | 120 | | 5.354 | 5.382 |
| 91 | C10/-2 | 109 | 110 | 123 | 137 | 138 | | 5.400 | 6.100 |
| 92 | C10= | 69 | 83 | 97 | 111 | 125 | 140 | 5.400 | 6.210 |
| 93 | C10 | 57 | 71 | 85 | 99 | 113 | 142 | 5.400 | 6.112 |
| 94 | C3 Benzene | 91 | 92 | 105 | 119 | 120 | | 5.579 | 5.614 |
| 95 | C3 Benzene | 91 | 92 | 105 | 119 | 120 | | 5.637 | 5.732 |
| 96 | C3 Benzene | 91 | 92 | 105 | 119 | 120 | | 5.777 | 5.816 |
| 97 | C3 Benzene | 91 | 92 | 105 | 119 | 120 | | 5.873 | 5.934 |
| 98 | C4 Benzene | 91 | 92 | 105 | 106 | 119 | 134 | 5.982 | 6.023 |
| 99 | C4 Benzene | 91 | 92 | 105 | 106 | 119 | 134 | 6.071 | 6.107 |
| 100 | C3 Benzene | 91 | 92 | 105 | 119 | 120 | | 6.082 | 6.123 |
| 101 | C11= | 69 | 83 | 97 | 125 | 139 | 154 | 6.138 | 6.900 |
| 102 | C11 | 71 | 85 | 99 | 113 | 127 | 156 | 6.138 | 6.754 |
| 103 | Indane | 117 | 118 | | | | | 6.179 | 6.217 |
| 104 | Indene | 115 | 116 | | | | | 6.245 | 6.286 |

Complete Chemist's Rules for Mogas

| Rule[a] | Compound[b] | Masses[c] | | | | | | Retention Time[d] Start | End |
|---|---|---|---|---|---|---|---|---|---|
| 105 | C4 Benzene | 91 | 92 | 105 | 106 | 119 | 134 | 6.255 | 6.402 |
| 106 | C11/-2 | 81 | 95 | 109 | 123 | 137 | 152 | 6.400 | 6.750 |
| 107 | C4 Benzene | 91 | 92 | 105 | 106 | 119 | 134 | 6.434 | 6.558 |
| 108 | C11/-4 | 79 | 93 | 107 | 121 | 135 | 150 | 6.450 | 6.700 |
| 109 | C1 Indane | 104 | 117 | 118 | 131 | 145 | 146 | 6.479 | 6.545 |
| 110 | C4 Benzene | 91 | 92 | 105 | 106 | 119 | 134 | 6.627 | 6.745 |
| 111 | C12/-2 | 81 | 95 | 109 | 123 | 151 | 166 | 6.710 | 7.430 |
| 112 | C12= | 69 | 83 | 97 | 111 | 139 | 168 | 6.710 | 7.430 |
| 113 | C12 | 71 | 85 | 99 | 113 | 141 | 170 | 6.712 | 7.330 |
| 114 | C5 Benzene | 91 | 105 | 106 | 119 | 133 | 148 | 6.798 | 7.048 |
| 115 | C12/-4 | 93 | 107 | 121 | 135 | 149 | 164 | 6.800 | 7.430 |
| 116 | C2 Indane | 104 | 117 | 118 | 131 | 145 | 146 | 6.834 | 6.846 |
| 117 | C1 Indane | 104 | 117 | 118 | 131 | 145 | 146 | 6.836 | 6.941 |
| 118 | C1 Indene | 115 | 129 | 130 | | | | 6.903 | 6.973 |
| 119 | C13/-2 | 81 | 95 | 109 | 123 | 165 | 180 | 7.000 | 7.760 |
| 120 | C13= | 69 | 83 | 97 | 111 | 153 | 182 | 7.000 | 7.760 |
| 121 | C2 Indane | 104 | 117 | 118 | 131 | 145 | 146 | 7.089 | 7.207 |
| 122 | Naphthalene | 102 | 128 | | | | | 7.113 | 7.182 |
| 123 | C5 Benzene | 91 | 105 | 106 | 119 | 133 | 148 | 7.159 | 7.198 |
| 124 | Benzeneothiophene | 133 | 134 | | | | | 7.176 | 7.210 |
| 125 | C5 Benzene | 91 | 105 | 106 | 119 | 133 | 148 | 7.226 | 7.251 |
| 126 | C6 Benzene | 91 | 105 | 106 | 119 | 133 | 162 | 7.300 | 7.320 |
| 127 | MMT | 55 | 79 | 134 | 162 | 218 | | 7.300 | 7.820 |
| 128 | C6 Benzene | 91 | 105 | 106 | 119 | 133 | 162 | 7.366 | 7.500 |
| 129 | C2 Indane | 104 | 117 | 118 | 131 | 145 | 146 | 7.376 | 7.410 |
| 130 | C2 Indene | 115 | 129 | 143 | 144 | | | 7.400 | 7.604 |
| 131 | C2 Indane | 104 | 117 | 118 | 131 | 145 | 146 | 7.465 | 7.494 |
| 132 | C2 Indane | 104 | 117 | 118 | 131 | 145 | 146 | 7.547 | 7.587 |
| 133 | C3 Indene | 115 | 129 | 143 | 157 | 158 | | 7.600 | 7.730 |
| 134 | C5 Benzene | 91 | 105 | 106 | 119 | 133 | 148 | 7.631 | 7.652 |
| 135 | C13 | 71 | 85 | 99 | 113 | 155 | 184 | 7.645 | 7.660 |
| 136 | C2 Indane | 104 | 117 | 118 | 131 | 145 | 146 | 7.652 | 7.676 |
| 137 | C3 Indane | 117 | 131 | 145 | 159 | 160 | | 7.664 | 7.723 |
| 138 | C1 Benzothio | 147 | 148 | | | | | 7.701 | 7.849 |
| 139 | 2MeNaphthalene | 141 | 142 | | | | | 7.722 | 7.770 |
| 140 | 1MeNaphthalene | 141 | 142 | | | | | 7.820 | 7.861 |
| 141 | C2 Naphthalene | 141 | 142 | | | | | 8.283 | 8.382 |
| 142 | Phenanthrene | 178 | | | | | | 9.500 | 10.000 |

[a] Rule number, integer index
[b] Compound or group of compounds rule applies to, for example
C3= refers to olefin or cycloparaffin with 3 carbons
C5/-2 refers to diolefin, dicycloparaffin or cyclo-olefin with 5 carbons
C5/-4 refers to triolefin, tricycloparaffin, dicyclo-olefin, cyclodiolefin with a total of 5 carbons
C1Benzothio methyl substituted benzothiophene ($C_n/H_{2n-10}S$)
[c] Masses used in Rule [up to n may be specified, where n is an integer which is equal to the number of masses scanned during the time interval (d) either in full scan mode or selected ion monitoring mode].
[d] Retention time for both starting and ending retention times based on historical averages, in minutes

COMPLETE CHEMIST'S RULES FOR MOGAS WITH CORRECTIONS

Total Raw Abundance (TIC): 125963855
Chemist Rule: 80972353 (64.282%)
Air Leakage: 7201540 (5.717%)
Avg Scan Rate (Min/Max): 128 (126/215)
Number of Records: 4857

| Rule[a] | Compound[b] | Masses[c] | | | | Start[d] | End[e] | CStart[f] | Corr[g] | CEnd[h] | Corr[i] | Abundance[j] | Abundance[j] |
|---|---|---|---|---|---|---|---|---|---|---|---|---|---|
| 1 | C3= | 27 | 41 | 42 | | 1.560 | 1.590 | 1.551 | −0.009 | 1.581 | −0.009 | 0 | 0.00% |
| 2 | C3 | 29 | 43 | 44 | | 1.570 | 1.600 | 1.561 | −0.009 | 1.591 | −0.009 | 0 | 0.00% |
| 3 | iC4 | 29 | 43 | 58 | | 1.605 | 1.624 | 1.596 | −0.009 | 1.614 | −0.010 | 14233 | 0.02% |
| 4 | nC5 | 29 | 43 | 58 | | 1.624 | 1.680 | 1.614 | −0.010 | 1.670 | −0.010 | 715655 | 0.88% |
| 5 | C5= | 27 | 41 | 55 | 70 | 1.684 | 1.708 | 1.674 | −0.010 | 1.698 | −0.010 | 20805 | 0.03% |
| 6 | C5 | 29 | 43 | 57 | 72 | 1.705 | 1.739 | 1.695 | −0.010 | 1.730 | −0.009 | 1129596 | 1.40% |
| 7 | C5= | 27 | 41 | 55 | 70 | 1.736 | 1.772 | 1.727 | −0.009 | 1.763 | −0.009 | 780267 | 0.96% |
| 8 | C5 | 29 | 43 | 57 | 72 | 1.739 | 1.794 | 1.730 | −0.009 | 1.785 | −0.009 | 1189151 | 1.47% |
| 9 | C5= | 27 | 41 | 55 | 70 | 1.772 | 1.794 | 1.763 | −0.009 | 1.785 | −0.009 | 1097894 | 1.36% |
| 10 | C5/-2 | 39 | 53 | 68 | | 1.775 | 1.796 | 1.766 | −0.009 | 1.787 | −0.009 | 194465 | 0.24% |
| 11 | C5= | 27 | 41 | 55 | 70 | 1.794 | 1.840 | 1.785 | −0.009 | 1.831 | −0.009 | 1219014 | 1.51% |
| 12 | C5/-2 | 39 | 53 | 68 | | 1.796 | 1.839 | 1.787 | −0.009 | 1.830 | −0.009 | 213325 | 0.26% |
| 13 | C5/-2 | 39 | 53 | 68 | | 1.839 | 1.873 | 1.830 | −0.009 | 1.864 | −0.009 | 48362 | 0.06% |

-continued

COMPLETE CHEMIST'S RULES FOR MOGAS WITH CORRECTIONS

| | | | | | | | | | | | | | | | |
|---|---|---|---|---|---|---|---|---|---|---|---|---|---|---|---|
| 14 | C5/-4 | 39 | 40 | 65 | 66 | | | 1.856 | 1.882 | 1.847 | −0.009 | 1.873 | −0.009 | 35019 | 0.04% |
| 15 | C6= | 27 | 41 | 55 | 56 | 69 | 84 | 1.907 | 1.934 | 1.898 | −0.009 | 1.925 | −0.009 | 47825 | 0.06% |
| 16 | C6 | 29 | 43 | 57 | 71 | 86 | | 1.926 | 1.973 | 1.917 | −0.009 | 1.964 | −0.009 | 1586920 | 1.96% |
| 17 | C6= | 27 | 41 | 55 | 56 | 69 | 84 | 1.934 | 1.962 | 1.925 | −0.009 | 1.953 | −0.009 | 379986 | 0.47% |
| 18 | C5= | 27 | 41 | 55 | 70 | | | 1.945 | 1.969 | 1.936 | −0.009 | 1.960 | −0.009 | 813127 | 1.00% |
| 19 | C6= | 27 | 41 | 55 | 56 | 69 | 84 | 1.962 | 1.982 | 1.953 | −0.009 | 1.973 | −0.009 | 1160073 | 1.43% |
| 20 | C6 | 29 | 43 | 57 | 71 | 86 | | 1.998 | 2.032 | 1.989 | −0.009 | 2.023 | −0.009 | 810472 | 1.00% |
| 21 | C6= | 27 | 41 | 55 | 56 | 69 | 84 | 2.036 | 2.066 | 2.027 | −0.009 | 2.058 | −0.008 | 467971 | 0.58% |
| 22 | C6 | 29 | 43 | 57 | 71 | 86 | | 2.076 | 2.117 | 2.068 | −0.008 | 2.109 | −0.008 | 1112977 | 1.38% |
| 23 | C6= | 27 | 41 | 55 | 56 | 69 | 84 | 2.095 | 2.137 | 2.087 | −0.008 | 2.129 | −0.008 | 1269477 | 1.57% |
| 24 | C6= | 27 | 41 | 55 | 56 | 69 | 84 | 2.137 | 2.156 | 2.129 | −0.008 | 2.148 | −0.008 | 442930 | 0.55% |
| 25 | C6= | 29 | 41 | 55 | 56 | 69 | 84 | 2.156 | 2.178 | 2.148 | −0.008 | 2.170 | −0.008 | 421028 | 0.52% |
| 26 | C6/-2 | 41 | 53 | 67 | 82 | | | 2.159 | 2.186 | 2.151 | −0.008 | 2.178 | −0.008 | 161562 | 0.20% |
| 27 | C6= | 27 | 41 | 55 | 56 | 69 | 84 | 2.178 | 2.203 | 2.170 | −0.008 | 2.195 | −0.009 | 248065 | 0.31% |
| 28 | C6/-2 | 41 | 53 | 67 | 82 | | | 2.186 | 2.204 | 2.178 | −0.008 | 2.196 | −0.008 | 105786 | 0.13% |
| 29 | C6= | 27 | 41 | 55 | 56 | 69 | 84 | 2.203 | 2.244 | 2.195 | −0.008 | 2.236 | −0.008 | 447307 | 0.55% |
| 30 | C6= | 27 | 41 | 55 | 56 | 69 | 84 | 2.244 | 2.290 | 2.236 | −0.008 | 2.282 | −0.008 | 1057535 | 1.31% |
| 31 | C7 | 43 | 57 | 71 | 85 | 100 | | 2.252 | 2.276 | 2.244 | −0.008 | 2.268 | −0.008 | 160388 | 0.20% |
| 32 | C6= | 27 | 41 | 55 | 56 | 69 | 84 | 2.290 | 2.314 | 2.282 | −0.008 | 2.306 | −0.008 | 484444 | 0.60% |
| 33 | C6/-4 | 39 | 41 | 56 | 79 | 80 | | 2.357 | 2.384 | 2.349 | −0.008 | 2.377 | −0.007 | 18054 | 0.02% |
| 34 | C6/-4 | 39 | 41 | 56 | 79 | 80 | | 2.384 | 2.415 | 2.377 | −0.007 | 2.408 | −0.007 | 30534 | 0.04% |
| 35 | C6/-2 | 41 | 53 | 67 | 82 | | | 2.441 | 2.477 | 2.434 | −0.007 | 2.470 | −0.007 | 312982 | 0.39% |
| 36 | C7= | 41 | 55 | 69 | 70 | 83 | 98 | 2.467 | 2.487 | 2.460 | −0.007 | 2.480 | −0.007 | 105390 | 0.13% |
| 37 | C7= | 41 | 55 | 69 | 70 | 83 | 98 | 2.519 | 2.537 | 2.512 | −0.007 | 2.530 | −0.007 | 48309 | 0.06% |
| 38 | Benzene | 78 | | | | | | 2.521 | 2.590 | 2.514 | −0.007 | 2.583 | −0.007 | 456913 | 0.56% |
| 39 | C6= | 27 | 41 | 55 | 56 | 69 | 84 | 2.524 | 2.562 | 2.517 | −0.007 | 2.555 | −0.007 | 155038 | 0.19% |
| 40 | C7 | 43 | 57 | 71 | 85 | 100 | | 2.554 | 2.611 | 2.547 | −0.007 | 2.604 | −0.007 | 1413849 | 1.75% |
| 41 | C7= | 41 | 55 | 69 | 70 | 83 | 98 | 2.571 | 2.610 | 2.564 | −0.007 | 2.603 | −0.007 | 600947 | 0.74% |
| 42 | C7 | 43 | 57 | 71 | 85 | 100 | | 2.645 | 2.684 | 2.638 | −0.007 | 2.678 | −0.006 | 1094972 | 1.35% |
| 43 | C8 | 39 | 41 | 56 | 83 | 99 | 114 | 2.740 | 2.870 | 2.734 | −0.006 | 2.865 | −0.005 | 1910679 | 2.36% |
| 44 | C7= | 41 | 55 | 69 | 70 | 83 | 98 | 2.742 | 2.868 | 2.736 | −0.006 | 2.863 | −0.005 | 1307310 | 1.62% |
| 45 | C7 | 43 | 57 | 71 | 85 | 100 | | 2.771 | 2.793 | 2.765 | −0.006 | 2.787 | −0.006 | 236375 | 0.29% |
| 46 | C7= | 41 | 55 | 69 | 70 | 83 | 98 | 2.911 | 3.141 | 2.906 | −0.005 | 3.137 | −0.004 | 1121554 | 1.39% |
| 47 | C7 | 43 | 57 | 71 | 85 | 100 | | 2.928 | 2.976 | 2.923 | −0.005 | 2.971 | −0.005 | 823658 | 1.02% |
| 48 | C7/-2 | 39 | 53 | 67 | 81 | 96 | | 2.978 | 3.025 | 2.973 | −0.005 | 3.020 | −0.005 | 203121 | 0.25% |
| 49 | C7/-2 | 39 | 53 | 67 | 81 | 96 | | 3.137 | 3.167 | 3.133 | −0.004 | 3.163 | −0.004 | 64492 | 0.08% |
| 50 | C7= | 41 | 55 | 69 | 70 | 83 | 98 | 3.168 | 3.198 | 3.164 | −0.004 | 3.194 | −0.004 | 100858 | 0.13% |
| 51 | C7= | 41 | 55 | 69 | 70 | 83 | 98 | 3.246 | 3.300 | 3.242 | −0.004 | 3.297 | −0.003 | 624082 | 0.77% |
| 52 | C8 | 43 | 57 | 71 | 85 | 99 | 114 | 3.351 | 3.446 | 3.348 | −0.003 | 3.443 | −0.003 | 700278 | 0.87% |
| 53 | C8 | 43 | 57 | 71 | 85 | 99 | 114 | 3.369 | 3.422 | 3.366 | −0.003 | 3.419 | −0.003 | 672534 | 0.83% |
| 54 | C8= | 41 | 55 | 69 | 83 | 97 | 112 | 3.371 | 3.396 | 3.368 | −0.003 | 3.393 | −0.003 | 71932 | 0.09% |
| 55 | C7= | 41 | 55 | 69 | 70 | 83 | 98 | 3.409 | 3.437 | 3.406 | −0.003 | 3.434 | −0.003 | 292860 | 0.36% |
| 56 | C8= | 41 | 55 | 69 | 83 | 97 | 112 | 3.487 | 3.509 | 3.484 | −0.003 | 3.507 | −0.002 | 77610 | 0.10% |
| 57 | C7/-2 | 39 | 53 | 67 | 81 | 96 | | 3.488 | 3.508 | 3.485 | −0.003 | 3.506 | −0.002 | 37349 | 0.05% |
| 58 | C7/-4 | 41 | 56 | 79 | 93 | 94 | | 3.530 | 3.550 | 3.528 | −0.002 | 3.548 | −0.002 | 12506 | 0.02% |
| 59 | C8= | 41 | 55 | 69 | 83 | 97 | 112 | 3.582 | 3.605 | 3.580 | −0.002 | 3.603 | −0.002 | 106300 | 0.13% |
| 60 | C8 | 43 | 55 | 57 | 71 | 99 | 114 | 3.585 | 3.661 | 3.583 | −0.002 | 3.659 | −0.002 | 947376 | 1.17% |
| 61 | C7/-4 | 41 | 56 | 79 | 93 | 94 | | 3.590 | 3.710 | 3.588 | −0.002 | 3.708 | −0.002 | 191500 | 0.24% |
| 62 | C8 | 43 | 57 | 71 | 85 | 99 | 114 | 3.610 | 3.622 | 3.608 | −0.002 | 3.620 | −0.002 | 453814 | 0.56% |
| 63 | C8 | 43 | 57 | 70 | 71 | 85 | 99 | 114 | 3.661 | 3.721 | 3.659 | −0.002 | 3.720 | −0.001 | 780121 | 0.96% |
| 64 | C7/-2 | 39 | 53 | 67 | 81 | 96 | | 3.676 | 3.727 | 3.674 | −0.002 | 3.726 | −0.001 | 202854 | 0.25% |
| 65 | C8 | 43 | 57 | 71 | 85 | 99 | 114 | 3.734 | 3.791 | 3.733 | −0.001 | 3.790 | −0.001 | 231822 | 0.29% |
| 66 | C8= | 41 | 55 | 69 | 83 | 97 | 112 | 3.789 | 3.817 | 3.788 | −0.001 | 3.816 | −0.001 | 83481 | 0.10% |
| 67 | C8 | 43 | 57 | 71 | 85 | 99 | 114 | 3.805 | 3.940 | 3.804 | −0.001 | 3.940 | 0.000 | 1033435 | 1.28% |
| 68 | Toluene | 91 | 92 | | | | | 3.810 | 3.915 | 3.809 | −0.001 | 3.915 | 0.000 | 7948033 | 9.82% |
| 69 | C7/-2 | 39 | 53 | 67 | 81 | 96 | | 3.874 | 3.899 | 3.873 | −0.001 | 3.899 | 0.000 | 51218 | 0.06% |
| 70 | C8= | 41 | 55 | 69 | 83 | 97 | 112 | 3.912 | 3.990 | 3.912 | 0.000 | 3.991 | 0.001 | 403062 | 0.50% |
| 71 | C8= | 41 | 55 | 69 | 83 | 97 | 112 | 4.062 | 4.318 | 4.064 | 0.002 | 4.324 | 0.006 | 932003 | 1.15% |
| 72 | C8/-2 | 39 | 53 | 67 | 81 | 95 | 110 | 4.167 | 4.181 | 4.171 | 0.004 | 4.185 | 0.004 | 33396 | 0.04% |
| 73 | C8 | 43 | 57 | 71 | 85 | 99 | 114 | 4.191 | 4.221 | 4.195 | 0.004 | 4.226 | 0.005 | 270706 | 0.33% |
| 74 | C8/-2 | 39 | 53 | 67 | 81 | 95 | 110 | 4.299 | 4.325 | 4.305 | 0.006 | 4.331 | 0.006 | 92852 | 0.12% |
| 75 | C8= | 41 | 55 | 69 | 83 | 97 | 112 | 4.491 | 4.559 | 4.500 | 0.009 | 4.569 | 0.010 | 262214 | 0.32% |
| 76 | C9= | 41 | 69 | 83 | 97 | 111 | 126 | 4.492 | 4.588 | 4.501 | 0.009 | 4.598 | 0.011 | 283866 | 0.35% |
| 77 | C9 | 43 | 71 | 85 | 99 | 113 | 128 | 4.492 | 4.508 | 4.501 | 0.009 | 4.517 | 0.009 | 38948 | 0.05% |
| 78 | C9 | 43 | 71 | 85 | 99 | 113 | 128 | 4.556 | 4.578 | 4.566 | 0.010 | 4.588 | 0.010 | 48572 | 0.06% |
| 79 | C8/-2 | 39 | 53 | 67 | 81 | 95 | 110 | 4.590 | 4.605 | 4.601 | 0.011 | 4.616 | 0.011 | 15446 | 0.02% |
| 80 | C9= | 41 | 69 | 83 | 97 | 111 | 126 | 4.645 | 4.936 | 4.656 | 0.011 | 4.952 | 0.016 | 401171 | 0.50% |
| 81 | Et Benzene | 91 | 105 | 106 | | | | 4.804 | 4.856 | 4.818 | 0.014 | 4.871 | 0.015 | 1755888 | 2.17% |
| 82 | C9 | 43 | 71 | 85 | 99 | 113 | 128 | 4.836 | 4.870 | 4.850 | 0.014 | 4.885 | 0.015 | 180884 | 0.22% |
| 83 | m + p-Xylene | 91 | 105 | 106 | | | | 4.877 | 4.956 | 4.892 | 0.015 | 4.972 | 0.016 | 6618720 | 8.17% |
| 84 | C9 | 43 | 71 | 85 | 99 | 113 | 128 | 4.906 | 4.925 | 4.921 | 0.015 | 4.941 | 0.016 | 52748 | 0.07% |
| 85 | C9= | 41 | 69 | 83 | 97 | 111 | 126 | 4.972 | 5.084 | 4.988 | 0.016 | 5.100 | 0.016 | 183924 | 0.23% |
| 86 | o-Xylene | 91 | 105 | 106 | | | | 5.086 | 5.146 | 5.102 | 0.016 | 5.162 | 0.016 | 2736750 | 3.38% |
| 87 | C9= | 41 | 69 | 83 | 97 | 111 | 126 | 5.113 | 5.161 | 5.129 | 0.016 | 5.177 | 0.016 | 112279 | 0.14% |
| 88 | C9 | 43 | 71 | 85 | 99 | 113 | 128 | 5.138 | 5.159 | 5.154 | 0.016 | 5.175 | 0.016 | 78032 | 0.10% |
| 89 | C9= | 41 | 69 | 83 | 97 | 111 | 126 | 5.211 | 5.459 | 5.226 | 0.015 | 5.474 | 0.015 | 214003 | 0.26% |

| | COMPLETE CHEMIST'S RULES FOR MOGAS WITH CORRECTIONS | | | | | | | | | | | | | |
|---|---|---|---|---|---|---|---|---|---|---|---|---|---|---|
| 90 | C3 Benzene | 91 | 92 | 105 | 119 | 120 | | 5.354 | 5.382 | 5.369 | 0.015 | 5.397 | 0.015 | 92133 | 0.11% |
| 91 | C10/-2 | 109 | 110 | 123 | 137 | 138 | | 5.400 | 6.100 | 5.415 | 0.015 | 6.115 | 0.015 | 0 | 0.00% |
| 92 | C10= | 69 | 83 | 97 | 111 | 125 | 140 | 5.400 | 6.210 | 5.415 | 0.015 | 6.225 | 0.015 | 379745 | 0.47% |
| 93 | C10 | 57 | 71 | 85 | 99 | 113 | 142 | 5.400 | 6.112 | 5.415 | 0.015 | 6.127 | 0.015 | 678126 | 0.84% |
| 94 | C3 Benzene | 91 | 92 | 105 | 119 | 120 | | 5.579 | 5.614 | 5.594 | 0.015 | 5.629 | 0.015 | 571333 | 0.71% |
| 95 | C3 Benzene | 91 | 92 | 105 | 119 | 120 | | 5.637 | 5.732 | 5.652 | 0.015 | 5.747 | 0.015 | 4268402 | 5.27% |
| 96 | C3 Benzene | 91 | 92 | 105 | 119 | 120 | | 5.777 | 5.816 | 5.792 | 0.015 | 5.831 | 0.015 | 778193 | 0.96% |
| 97 | C3 Benzene | 91 | 92 | 105 | 119 | 120 | | 5.873 | 5.934 | 5.888 | 0.015 | 5.949 | 0.015 | 3263117 | 4.03% |
| 98 | C4 Benzene | 91 | 92 | 105 | 106 | 119 | 134 | 5.982 | 6.023 | 5.997 | 0.015 | 6.038 | 0.015 | 60719 | 0.08% |
| 99 | C4 Benzene | 91 | 92 | 105 | 106 | 119 | 134 | 6.071 | 6.107 | 6.086 | 0.015 | 6.122 | 0.015 | 497424 | 0.61% |
| 100 | C3 Benzene | 91 | 92 | 105 | 119 | 120 | | 6.082 | 6.123 | 6.097 | 0.015 | 6.138 | 0.015 | 776999 | 0.96% |
| 101 | C11= | 69 | 83 | 97 | 125 | 139 | 154 | 6.138 | 6.900 | 6.153 | 0.015 | 6.915 | 0.015 | 166061 | 0.21% |
| 102 | C11 | 71 | 85 | 99 | 113 | 127 | 156 | 6.138 | 6.754 | 6.153 | 0.015 | 6.769 | 0.015 | 324662 | 0.40% |
| 103 | Indane | 117 | 118 | | | | | 6.179 | 6.217 | 6.194 | 0.015 | 6.232 | 0.015 | 382862 | 0.47% |
| 104 | Indene | 115 | 116 | | | | | 6.245 | 6.286 | 6.260 | 0.015 | 6.301 | 0.015 | 60477 | 0.08% |
| 105 | C4 Benzene | 91 | 92 | 105 | 106 | 119 | 134 | 6.255 | 6.402 | 6.270 | 0.015 | 6.417 | 0.015 | 1817904 | 2.25% |
| 106 | C11/-2 | 81 | 95 | 109 | 123 | 137 | 152 | 6.400 | 6.750 | 6.415 | 0.015 | 6.765 | 0.015 | 0 | 0.00% |
| 107 | C4 Benzene | 91 | 92 | 105 | 106 | 119 | 134 | 6.434 | 6.558 | 6.449 | 0.015 | 6.573 | 0.015 | 1317323 | 1.63% |
| 108 | C11/-4 | 79 | 93 | 107 | 121 | 135 | 150 | 6.450 | 6.700 | 6.465 | 0.015 | 6.715 | 0.015 | 42140 | 0.05% |
| 109 | Me Indane | 104 | 117 | 131 | 132 | | | 6.479 | 6.545 | 6.494 | 0.015 | 6.560 | 0.015 | 296319 | 0.37% |
| 110 | C4 Benzene | 91 | 92 | 105 | 106 | 119 | 134 | 6.627 | 6.745 | 6.642 | 0.015 | 6.760 | 0.015 | 1013676 | 1.25% |
| 111 | C12/-2 | 81 | 95 | 109 | 123 | 151 | 166 | 6.710 | 7.430 | 6.725 | 0.015 | 7.449 | 0.019 | 445 | 0.00% |
| 112 | C12= | 69 | 83 | 97 | 111 | 139 | 168 | 6.710 | 7.430 | 6.725 | 0.015 | 7.449 | 0.019 | 76201 | 0.09% |
| 113 | C12 | 71 | 85 | 99 | 113 | 141 | 170 | 6.712 | 7.330 | 6.727 | 0.015 | 7.347 | 0.017 | 181880 | 0.23% |
| 114 | C5 Benzene | 91 | 105 | 106 | 119 | 133 | 148 | 6.798 | 7.048 | 6.813 | 0.015 | 7.063 | 0.015 | 1158186 | 1.43% |
| 115 | C12/-4 | 93 | 107 | 121 | 135 | 149 | 164 | 6.800 | 7.430 | 6.815 | 0.015 | 7.449 | 0.019 | 6694 | 0.01% |
| 116 | C2 Indane | 104 | 117 | 118 | 131 | 145 | 146 | 6.834 | 6.846 | 6.849 | 0.015 | 6.861 | 0.015 | 65467 | 0.08% |
| 117 | Me Indane | 104 | 117 | 131 | 132 | | | 6.836 | 6.941 | 6.851 | 0.015 | 6.956 | 0.015 | 725115 | 0.90% |
| 118 | Me Indene | 115 | 129 | 130 | | | | 6.903 | 6.973 | 6.918 | 0.015 | 6.988 | 0.015 | 227195 | 0.28% |
| 119 | C13/-2 | 81 | 95 | 109 | 123 | 165 | 180 | 7.000 | 7.760 | 7.015 | 0.015 | 7.784 | 0.024 | 0 | 0.00% |
| 120 | C13= | 69 | 83 | 97 | 111 | 153 | 182 | 7.000 | 7.760 | 7.015 | 0.015 | 7.784 | 0.024 | 82801 | 0.10% |
| 121 | C2 Indane8 | 104 | 117 | 118 | 131 | 145 | 146 | 7.089 | 7.207 | 7.104 | 0.015 | 7.222 | 0.016 | 430159 | 0.53% |
| 122 | Naphthalene | 102 | 128 | | | | | 7.113 | 7.182 | 7.128 | 0.015 | 7.197 | 0.015 | 680168 | 0.84% |
| 123 | C5 Benzene | 91 | 105 | 106 | 119 | 133 | 148 | 7.159 | 7.198 | 7.174 | 0.015 | 7.213 | 0.015 | 214964 | 0.27% |
| 124 | Benzothiophene | 133 | 134 | | | | | 7.176 | 7.210 | 7.191 | 0.015 | 7.226 | 0.016 | 117429 | 0.15% |
| 125 | C5 Benzene | 91 | 105 | 106 | 119 | 133 | 148 | 7.226 | 7.251 | 7.242 | 0.016 | 7.267 | 0.016 | 74124 | 0.09% |
| 126 | C6 Benzene | 91 | 105 | 106 | 119 | 133 | 162 | 7.300 | 7.320 | 7.317 | 0.017 | 7.337 | 0.017 | 69597 | 0.09% |
| 127 | MMT | 55 | 79 | 134 | 162 | 218 | | 7.300 | 7.820 | 7.317 | 0.017 | 7.844 | 0.024 | 82401 | 0.10% |
| 128 | C6 Benzene | 91 | 105 | 106 | 119 | 133 | 162 | 7.366 | 7.500 | 7.384 | 0.018 | 7.520 | 0.020 | 260793 | 0.32% |
| 129 | C2/-8 | 104 | 117 | 118 | 131 | 145 | 146 | 7.376 | 7.410 | 7.394 | 0.018 | 7.429 | 0.019 | 144073 | 0.18% |
| 130 | C2 Indene | 115 | 129 | 143 | 144 | | | 7.400 | 7.604 | 7.419 | 0.019 | 7.626 | 0.022 | 185620 | 0.23% |
| 131 | C2 Indane | 104 | 117 | 118 | 131 | 145 | 146 | 7.465 | 7.494 | 7.485 | 0.020 | 7.514 | 0.020 | 148372 | 0.18% |
| 132 | C2 Indane | 104 | 117 | 118 | 131 | 145 | 146 | 7.547 | 7.587 | 7.568 | 0.021 | 7.609 | 0.022 | 136473 | 0.17% |
| 133 | C3 Indene | 115 | 129 | 143 | 157 | 158 | | 7.600 | 7.730 | 7.622 | 0.022 | 7.754 | 0.024 | 58298 | 0.07% |
| 134 | C5 Benzene | 91 | 105 | 106 | 119 | 133 | 148 | 7.631 | 7.652 | 7.653 | 0.022 | 7.675 | 0.023 | 42922 | 0.05% |
| 135 | C13 | 71 | 85 | 99 | 113 | 155 | 184 | 7.645 | 7.660 | 7.668 | 0.023 | 7.683 | 0.023 | 36141 | 0.05% |
| 136 | C2 Indane/-8 | 104 | 117 | 118 | 131 | 145 | 146 | 7.652 | 7.676 | 7.675 | 0.023 | 7.699 | 0.023 | 72406 | 0.09% |
| 137 | C3 | 117 | 131 | 145 | 159 | 160 | | 7.664 | 7.723 | 7.687 | 0.023 | 7.747 | 0.024 | 96291 | 0.12% |

COMPLETE CHEMIST'S RULES FOR MOGAS WITH CORRECTIONS -continued

| | | | | | | | | | | | | |
|---|---|---|---|---|---|---|---|---|---|---|---|---|
| 138 | Indene C1Benzothio | 145 | 147 | 148 | | 7.701 | 7.849 | 7.724 | 0.023 | 7.873 | 0.024 | 255718 | 0.32% |
| 139 | 2Me Naphthalene | 141 | 142 | | | 7.722 | 7.770 | 7.746 | 0.024 | 7.794 | 0.024 | 1030117 | 1.27% |
| 140 | 1Me-Naphthalene | 141 | 142 | | | 7.820 | 7.861 | 7.844 | 0.024 | 7.885 | 0.024 | 410403 | 0.51% |
| 141 | C2 Naphthalene | 141 | 156 | | | 8.283 | 8.382 | 8.307 | 0.024 | 8.406 | 0.024 | 39022 | 0.05% |
| 142 | Phenanthrene | 178 | | | | 9.500 | 10.00 | 9.524 | 0.024 | 10.024 | 0.024 | 0 | 0.00% |
| | Sum = | | | | | | | | | | | 80972353 | 100.00% |

[a] Rule number, integer index
[b] Compound or group of compounds rule applies to, for example
C3= refers to olefin or cycloparaffin with 3 carbons
C5/-2 refers to diolefin, dicycloparaffin or cyclo-olefin with 5 carbons
C5/-4 refers to triolefin, tricycloparaffin, dicyclo-olefin, cyclodiolefin with a total of 5 carbons
C1Benzothiophene methyl substituted benzothiophene ($C_n/H_{2n-10}S$)
[c] Masses used in Rule [up to n may be specified, where n is an integer which is equal to the number of masses scanned during the time interval (d to e) either in full scan mode or selected ion monitoring mode].
[d] start retention time in minutes
[e] end retention time in minutes
[f] corrected start retention time, in minutes
[g] correction = difference between start and cstart (in minutes)
[h] corrected end time, in minutes
[i] correction = difference between end and cend (in minutes)
[j] Abundance, both as total sum and as normalized percentage based on Chemist's Rules.

What is claimed is:

1. A method for controlling the blending of a plurality of blend stocks each having boiling points less than about 350° C. into at least one blend product which comprises the steps of:

(a) selecting at least one of physical, perceptual, performance and chemical properties of at least one of blend stock and blend product;

(b) selecting reference samples, said reference samples containing characteristic compounds present in at least one blend stock and blend product and which have known values of the properties selected in the step (a);

(c) producing a training set by the steps of:

(1) injecting each reference sample into a gas chromatograph which is interfaced to a mass spectrometer thereby causing at least a partial separation of the hydrocarbon mixture into constituent chemical components;

(2) introducing the constituent chemical components of each said reference sample into the mass spectrometer, under dynamic flow conditions;

(3) obtaining for each said reference sample a series of time resolved mass chromatograms;

(4) calibrating the mass chromatograms to correct retention times;

(5) selecting a series of corrected retention time windows;

(6) selecting within each retention time window a series of molecular or fragment ions, said ions being representative of said characteristic compounds or compound classes expected within the retention time window;

(7) recording the total amount of each characteristic compound or compound group selected in the step c(6);

(8) forming the data from the steps c(6) and c(7) into a X-block matrix;

(9) forming the property data selected in the step (a) for said reference samples selected in the step (b) into a Y-block matrix;

(10) analyzing the data from the steps c(9) by multivariate correlation techniques including Partial Least Squares, Principal Component Regression, or Ridge Regression to produce a series of coefficients;

(d) subjecting at least one of said blend stock and said blend product samples to the steps c(1) and c(3) in the same manner as the reference sample to produce a series of time resolved mass chromatograms;

(e) repeating the steps c(4) to c(8) chromatograms from the step (d);

(f) multiplying the matrix from the step (e) by the coefficients from the step c(10) to produce a predicted value of the properties for the at least one of said blend stock and said blend product samples; and (g) using the predicted values of said selected properties of the at least one of said blend stock and said blend product samples to control the amount of said blend stock in the blend product.

2. A method for controlling or monitoring chemical or refinery processes which utilize feed stocks and/or produce products having boiling points less than abut 350° C. which comprises the steps of:

(a) selecting at least one of physical, perceptual, performance and chemical properties of at least one feed stock, intermediate stream and process product.

(b) selecting reference samples, said reference samples containing characteristic compounds present in the at least one said feed stock, intermediate stream or product and which have known values of the properties selected in the step (a);

(c) producing a training set by the steps of:

(1) injecting each said reference sample into a gas chromatograph which is interfaced to a mass spectrometer thereby causing at least a partial separation of the hydrocarbon mixture into constituent chemical components;

(2) introducing the constituent chemical components of each said reference sample into the mass spectrometer, under dynamic flow conditions;

(3) obtaining for each said reference sample a series of time resolved mass chromatograms;

(4) calibrating the mass chromatograms to correct retention times;

(5) selecting a series of corrected retention time windows;

(6) selecting within each retention time window a series of molecular and/or fragment ions, said ions being representative of said characteristic compounds or compound classes expected within the retention time window;

(7) recording the total amount of each characteristic compound or compound group selected in the step c(6);

(8) forming the data from the steps c(6) and c(7) into a X-block matrix;

(9) forming the property data selected in the step (a) for said reference samples selected in the step (b) into a Y-block matrix;

(10) analyzing the data from the steps c(9) by multivariate correlation techniques including Partial Least Squares, Principal Component Regression, or Ridge Regression to produce a series of coefficients;

(d) subjecting at least one of said refinery process chemical process, intermediate stream, product and feed stock sample to the steps c(1) to c(3) in the same manner as the reference sample to produce a series of time resolved mass chromatograms;

(e) repeating the steps c(4) to c(8) mass chromatograms from the step (d);

(f) multiplying the matrix from the step (e) by the coefficients from the step c(10) to produce a predicted value of the properties of the refinery or chemical sample or samples; and (g) using the predicted values of the properties of the refinery or chemical sample or samples to control the refinery or chemical process.

3. The method of claims 1 or 2 wherein the gas chromatograph is a capillary gas chromatograph and the mass spectrometer is a quadrupole mass spectrometer.

4. The method of claims 1 or 2 wherein the gas chromatograph and mass spectrometer are operated under repeatable conditions.

5. The method of claims 1 or 2 wherein the selection of a series of molecular and/or fragment ions characteristic of compounds or compound classes is accomplished using Chemist's Rules.

6. The method of claims 1 or 2 wherein the selection of a series of molecular and/or fragment ions characteristic of compounds or compound classes is accomplished using Hydrocarbon Type Analysis.

7. The method of claims 1 or 2 wherein data from the gas chromatograph and mass spectrometer are stored in a computer.

8. The method of claims i or 2 wherein data from the steps (c) to (f) are treated in a computer.

9. The method of claims 1 or 2 wherein other performance, perceptual, chemical or physical properties of the hydrocarbon mixture are selected.

10. The method of claims 1 or 2 wherein the data are collinear.

11. The method of claim 1 wherein the multivariate correlation technique is said Partial Least Squares.

* * * * *